US011944657B2

(12) United States Patent
Fujiwara et al.

(10) Patent No.: US 11,944,657 B2
(45) Date of Patent: Apr. 2, 2024

(54) AGENT FOR INDUCING INTERFERON PRODUCTION CONTAINING LACTIC ACID BACTERIA

(71) Applicant: KIRIN HOLDINGS KABUSHIKI KAISHA, Tokyo (JP)

(72) Inventors: Daisuke Fujiwara, Kanagawa (JP); Kenta Jonai, Kanagawa (JP); Tetsu Sugimura, Kanagawa (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 21 days.

(21) Appl. No.: 17/548,904

(22) Filed: Dec. 13, 2021

(65) Prior Publication Data

US 2022/0105140 A1    Apr. 7, 2022

Related U.S. Application Data

(60) Division of application No. 16/290,581, filed on Mar. 1, 2019, now Pat. No. 11,224,623, which is a division of application No. 15/367,649, filed on Dec. 2, 2016, now Pat. No. 10,220,060, which is a division of application No. 14/263,306, filed on Apr. 28, 2014, now Pat. No. 9,549,956, which is a continuation of application No. 13/977,435, filed as application No. PCT/JP2011/080359 on Dec. 28, 2011, now abandoned.

(30) Foreign Application Priority Data

Dec. 28, 2010 (JP) ................. 2010-293810

(51) Int. Cl.
| | |
|---|---|
| *A61K 35/744* | (2015.01) |
| *A23C 9/123* | (2006.01) |
| *A23C 19/032* | (2006.01) |
| *A23C 19/06* | (2006.01) |
| *A23L 33/135* | (2016.01) |
| *A61K 9/00* | (2006.01) |
| *A61K 31/711* | (2006.01) |
| *A61K 35/747* | (2015.01) |
| *C12N 1/20* | (2006.01) |
| *C12N 15/74* | (2006.01) |
| *C12Q 1/6809* | (2018.01) |
| *C12R 1/01* | (2006.01) |
| *G01N 33/68* | (2006.01) |

(52) U.S. Cl.
CPC ............ *A61K 35/744* (2013.01); *A23C 9/123* (2013.01); *A23C 9/1236* (2013.01); *A23C 19/0323* (2013.01); *A23C 19/062* (2013.01); *A23L 33/135* (2016.08); *A61K 9/0053* (2013.01); *A61K 31/711* (2013.01); *A61K 35/747* (2013.01); *C12N 1/20* (2013.01); *C12N 1/205* (2021.05); *C12N 15/746* (2013.01); *C12Q 1/6809* (2013.01); *G01N 33/6866* (2013.01); *A23V 2400/231* (2023.08); *C12R 2001/01* (2021.05)

(58) Field of Classification Search
CPC .. A61K 35/744; A61K 9/0053; A61K 31/711; A61K 35/747; A23L 33/135; C12N 1/205; C12N 1/20; C12N 15/746; A23C 9/123; A23C 9/1236; A23C 9/062; C12Q 1/6809; G01N 33/6866; C12R 1/01; A23Y 2240/41
See application file for complete search history.

(56) References Cited

U.S. PATENT DOCUMENTS

| | | | |
|---|---|---|---|
| 6,486,132 B2 | 11/2002 | Murata et al. | |
| 2010/0086988 A1 | 4/2010 | Shimizu et al. | |
| 2010/0266725 A1 | 10/2010 | Shimizu et al. | |
| 2011/0189343 A1 | 8/2011 | Hasegawa et al. | |

FOREIGN PATENT DOCUMENTS

| | | |
|---|---|---|
| EP | 0 599 479 A2 | 6/1994 |
| EP | 1538198 A2 | 6/2005 |
| JP | 2000-262247 | 9/2000 |

(Continued)

OTHER PUBLICATIONS

"Shokuhin to Kaihatsu (Food Processing and Ingredients)", May 1, 2007, vol. 42, No. 5, pp. 85-87.
Database WPI Week 200613, AN 2006-121971 & JP 2006 028047 A, Kikkoman Corp., Feb. 2, 2006, one page.
Database WPI Week 201003, An 2009-S57559 & JP 2009 296910 A, Morinaga Milk Ind. Co., Ltd., Dec. 24, 2009, one page.
Enomoto A, et al., "Differential effects of lactic acid bacteria on cytokine responses of splenocytes derived from SKG mice", Proceedings of the Japanese Society for Immunology, Nov. 5, 2008 (Nov. 5, 2008), vol. 38, p. 174 (2G-W29-11-P).

(Continued)

*Primary Examiner* — Robert A Zeman
(74) *Attorney, Agent, or Firm* — Foley & Lardner LLP

(57) ABSTRACT

This invention provides an IFN inducer comprising, as an active ingredient, lactic acid bacteria and capable of inducing IFN production, an immunopotentiating agent or prophylactic agent against virus infection comprising such inducer, and a food or drink product comprising such IFN inducer and having IFN-inducing activity, immunopotentiating activity, or prophylactic activity against virus infection. The agent for inducing IFN production comprises, as active ingredients, lactic acid bacteria that can activate plasmacytoid dendritic cells (pDCs) and promote IFN production, such as *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, or *Streptococcus thermophilus* TA-45.

2 Claims, 45 Drawing Sheets

(56) References Cited

FOREIGN PATENT DOCUMENTS

| JP | 2001-046020 | | 2/2001 |
|---|---|---|---|
| JP | 2006-028047 | | 2/2006 |
| JP | 2007-117031 | A | 5/2007 |
| JP | 2009-112205 | A | 5/2009 |
| JP | 2009-296910 | A1 | 12/2009 |
| JP | 2009-296972 | | 12/2009 |
| WO | WO 2008/099544 | A1 | 8/2008 |
| WO | WO-2009/005123 | | 1/2009 |
| WO | WO-2009/005124 | A1 | 1/2009 |
| WO | WO-2009/007515 | A1 | 1/2009 |
| WO | WO 2009/150897 | A1 | 12/2009 |
| WO | WO 2009/157073 | A1 | 12/2009 |
| WO | WO-2011/045471 | A1 | 4/2011 |

OTHER PUBLICATIONS

European Office Action dated Sep. 28, 2015, in corresponding EP 11853409.8.
Fukui, Y. et al.: Abstracts for the Annual Meeting of Japanese Association for Food Immunology, Oct. 23-24, 2006.
Hagi et al., "Screening and Characterization of Potential Probiotic Lactic Acid Bacteria from Cultured Common Carp Intestine," Biosci. Biotechnol. Biochem., 2009, 73(7):1479-1483.
Izumo et al., "Effect of intranasal administration of Lactobacillus pentosus S-PT84 on influenza virus infection in mice," International Immunopharmacology, 2010, 10:1101-1106.
Japanese Office Action dated Oct. 13, 2015, in corresponding JP 2012-551033.
Kawashima, T. et al.: Abstracts for the Annual Meeting of the Japan Society for Lactic Acid Bacteria, Jul. 26-27, 2010.
Kenta Jonai et al., "Virus Kansen Bogyo o Ninau Plasmacytoid Jujo Saibo o Kasseika suru Nyusankin no Hakken 2", Japan Society for Bioscience, Biotechnology, and Agrochemistry Taikai Koen Yoshishu, Mar. 5, 2011, vol. 2011, p. 215 (3J14p16).
Kenta JONAI et al., "Virus Kansen Bogyo o Ninau Plasmacytoid Jujo Saibo o Kasseika suru Nyusankin no Hakken 1", Japan Society for Bioscience, Biotechnology, and Agrochemistry Taikai Koen Yoshishu, Mar. 5, 2011, vol. 2011, p. 215 (3j14P15).
Kenta Jonia et al., "Virus Kansen Bogyo o Ninau Plasmacytoid Jujo Saibo o Kasseika suru Nyusankin No. Hakken 2", Japan Society for Bioscience, Biotechnology, and Agrochemistry Taikai Koen Yoshishu, Mar. 5, 2011, vol. 2011, p. 215 (3J14p16).
Kimoto-Nira H, et al., Anti-ageing effect of a lactococcal strain: analysis using senescence-accelerated mice, British Journal of Nutrition, Dec. 2007, vol. 98, No. 6, p. 1178-1186.

Kotenko, S. et al. "IFN-s mediate antiviral protection through a distinct class II cytokine receptor complex", Nature Immunology, Jan. 2003, vol. 4, No. 1, pp. 69-77.
Lammers K, et al., "DNA derived from probiotic bacteria modulates human dendritic cell phenotype and function", Gastroenterology, Apr. 2004, vol. 126, No. 4, p. A517 (#T1815).
Lei H, et al., "Immunoprotection against influenza H5N1 virus by oral administration of enteric-coated recombinant Lactococcus lactis mini-capsules", Virology, Nov. 25, 2010, vol. 407, No. 2, p. 319-324.
Marcello, T. et al. "Interferons and Inhibit Heptatitis C Virus Replication with Distinct Signal Transduction and Gene Regulation Kinetics", Gastroenterology, 2006, vol. 131, pp. 1887-1898.
Marcello, T. et al. "Interferons and A Inhibit Heptatitis C Virus Replication with Distinct Signal Transduction and Gene Regulation Kinetics", Gastroenterology, 2006, vol. 131, pp. 1887-1898.
Megjugorac, N. et al. "IL-4 enhances IFN-1 (IL-29) production by plasmacytoid DCs via monocyte secretion of IL-1Ra", Blood, 2010, vol. 115, pp. 4185-4190.
Morrow, A. et al. "A Novel Role for IFN-Stimulated Gene Factor 3 II in IFN—Signaling and Induction of Antiviral Activity in Human Cells", The Journal of Immunology, 2011, vol. 186, pp. 1685-1693.
Office Action dated May 20, 2016, in EP 11853409.8.
PCT/JP2011/080359 International Search Report, dated Feb. 15, 2012.
Supplementary European Search Report dated May 13, 2014, in EP 11853409.8.
Toki S, et al., "Gene expression profiles in the plasmacytoid dendritic cells stimulated with Lactobacillus GG or *E. coli*", Journal of Allergy and Clinical Immunology, Jan. 2007, vol. 119, No. 1, p. S259 (#1013).
Toshiya Maruo et al., "*Lactococcus lactis* subsp. cremoris FC Kabu Gyunyu Hakkobutsu no Keiko Toyo ga Influenza Virus Kansen Model Mouse ni Oyobosu Eikyo", Proceedings of Japanese Society of Food Science and Technology, Sep. 1, 2010 (Sep. 1, 2010). vol. 57th, p. 106 (2Ep8).
Veckman, V. et al. "*Streptococcus pyogenes* activates human plasmacytoid and myeloid dendritic cells", Journal of Leukocyte Biology, Feb. 2008, vol. 83, pp. 296-304.
Zhang et al., "Improvement of Human Interferon Alpha Secretion by *Lactococcus lactis*," Biotechnol. Lett., Sep. 2010, 32(9):1271-1277.
Office Action dated Dec. 20, 2016, in JP 2016-004279.
Hiramatsu et al., "Influence of *Bifidobacterium* on tissues of the immune system when orally administered to mice," Meeting of Japan Society for Bioscience, Biotechnology, and Agrochemistry, Mar. 5, 2004, 215, 3A19p03, with English translation.
Boslego et al., Vaccines and Immunotherapy, 1991, Chapter 17, "Gonorrhea Vaccines,", p. 211.
Ellis, Ronald W., Ph.D., Vaccines, Plotkin et al., Eds., 1988, Chapter 29 "New Technologies for Making Vaccines," 568-574.

Fig. 1A

| Strain ID | Genera | Culture collection |
|---|---|---|
| JCM 1192 | *Bifidobacterium breve* | JCM |
| JCM 1217 | *Bifidobacterium longum* | JCM |
| JCM 1021 | *Lactobacillus acidophilus* | JCM |
| JCM 1023 | *Lactobacillus acidophilus* | JCM |
| JCM 1028 | *Lactobacillus acidophilus* | JCM |
| JCM 1032 | *Lactobacillus acidophilus* | JCM |
| JCM 1034 | *Lactobacillus acidophilus* | JCM |
| JCM 1038 | *Lactobacillus acidophilus* | JCM |
| JCM 1132 | *Lactobacillus acidophilus* | JCM |
| JCM 1229 | *Lactobacillus acidophilus* | JCM |
| IFO 3960 | *Lactobacillus brevis* | IFO |
| IFO 12005 | *Lactobacillus brevis* | IFO |
| IFO 12520 | *Lactobacillus brevis* | IFO |
| IFO 13109 | *Lactobacillus brevis* | IFO |
| IFO 13110 | *Lactobacillus brevis* | IFO |
| JCM 1059 | *Lactobacillus brevis* | JCM |
| IFO 12004 | *Lactobacillus casei* | IFO |
| JCM 1134 | *Lactobacillus casei* | JCM |
| JCM 8129 | *Lactobacillus casei* | JCM |
| NRIC 1916 | *Lactobacillus casei* | NRIC |
| NRIC 1917 | *Lactobacillus casei* | NRIC |
| NRIC 1936 | *Lactobacillus casei* | NRIC |
| NRIC 1937 | *Lactobacillus casei* | NRIC |
| NRIC 1941 | *Lactobacillus casei* | NRIC |
| NRIC 1942 | *Lactobacillus casei* | NRIC |
| NRIC 1944 | *Lactobacillus casei* | NRIC |
| NRIC 1945 | *Lactobacillus casei* | NRIC |
| NRIC 1946 | *Lactobacillus casei* | NRIC |
| NRIC 1963 | *Lactobacillus casei* | NRIC |
| NRIC 1981 | *Lactobacillus casei* | NRIC |
| JCM 1002 | *Lactobacillus delbrueckii subsp. bulgaricus* | JCM |
| JCM 1012 | *Lactobacillus delbrueckii subsp. bulgaricus* | JCM |
| NRIC 1962 | *Lactobacillus fermentum* | NRIC |
| JCM 1017 | *Lactobacillus gasseri* | JCM |
| JCM 1130 | *Lactobacillus gasseri* | JCM |
| JCM 1131 | *Lactobacillus gasseri* | JCM |
| JCM 2124 | *Lactobacillus gasseri* | JCM |
| JCM 5813 | *Lactobacillus gasseri* | JCM |
| JCM 5814 | *Lactobacillus gasseri* | JCM |
| JCM 8789 | *Lactobacillus gasseri* | JCM |
| JCM 8790 | *Lactobacillus gasseri* | JCM |
| JCM 1120 | *Lactobacillus helveticus* | JCM |
| JCM 1155 | *Lactobacillus ilgardii* | JCM |
| JCM 1022 | *Lactobacillus johnsonii* | JCM |
| JCM 2012 | *Lactobacillus johnsonii* | JCM |
| JCM 2122 | *Lactobacillus johnsonii* | JCM |
| JCM 5812 | *Lactobacillus johnsonii* | JCM |
| JCM 8791 | *Lactobacillus johnsonii* | JCM |
| JCM 8792 | *Lactobacillus johnsonii* | JCM |
| JCM 8793 | *Lactobacillus johnsonii* | JCM |
| JCM 5818 | *Lactobacillus kefiri* | JCM |
| NRIC 1968 | *Lactobacillus kimuchii* | NRIC |
| NRIC 1969 | *Lactobacillus kimuchii* | NRIC |
| NRIC 1970 | *Lactobacillus kimuchii* | NRIC |

Fig. 1B

| Strain ID | Genera | Culture collection |
|---|---|---|
| ATCC 25302 | Lactobacillus paracasei | ATCC |
| ATCC 25303 | Lactobacillus paracasei | ATCC |
| IFO 3533 | Lactobacillus paracasei | IFO |
| JCM 1053 | Lactobacillus paracasei | JCM |
| JCM 1109 | Lactobacillus paracasei | JCM |
| JCM 1111 | Lactobacillus paracasei | JCM |
| JCM 1133 | Lactobacillus paracasei | JCM |
| JCM 1161 | Lactobacillus paracasei | JCM |
| JCM 1163 | Lactobacillus paracasei | JCM |
| JCM 1172 | Lactobacillus paracasei | JCM |
| JCM 1181 | Lactobacillus paracasei | JCM |
| JCM 1556 | Lactobacillus paracasei | JCM |
| JCM 2123 | Lactobacillus paracasei | JCM |
| JCM 2769 | Lactobacillus paracasei | JCM |
| JCM 8131 | Lactobacillus paracasei | JCM |
| JCM 8132 | Lactobacillus paracasei | JCM |
| JCM 8133 | Lactobacillus paracasei | JCM |
| JCM 1558 | Lactobacillus pentosus | JCM |
| JCM 8333 | Lactobacillus pentosus | JCM |
| JCM 8334 | Lactobacillus pentosus | JCM |
| JCM 8335 | Lactobacillus pentosus | JCM |
| JCM 8336 | Lactobacillus pentosus | JCM |
| JCM 8337 | Lactobacillus pentosus | JCM |
| JCM 8338 | Lactobacillus pentosus | JCM |
| JCM 8339 | Lactobacillus pentosus | JCM |
| JCM 8340 | Lactobacillus pentosus | JCM |
| ATCC 8014 | Lactobacillus plantarum | ATCC |
| ATCC 14917 | Lactobacillus plantarum | ATCC |
| JCM 1149 | Lactobacillus plantarum | JCM |
| NRIC 1596 | Lactobacillus plantarum | NRIC |
| JCM 1112 | Lactobacillus reuteri | JCM |
| ATCC 53103 | Lactobacillus rhamnosus | ATCC |
| IFO 3425 | Lactobacillus rhamnosus | IFO |
| JCM 1136 | Lactobacillus rhamnosus | JCM |
| JCM 1157 | Lactobacillus sakei | JCM |
| JCM 1150 | Lactobacillus salivarius subsp.salicins | JCM |

Fig. 1C

| Strain ID | Genera | Culture collection |
|---|---|---|
| JCM 8723 | Enterococcus casseliflavus | JCM |
| JCM 8730 | Enterococcus malodoratus | JCM |
| NBRC 100934 | Lactococcus garvieae | NBRC |
| JCM 16167 | Lactococcus lactis subsp. cremoris | JCM |
| JCM 20076 | Lactococcus lactis subsp. cremoris | JCM |
| NBRC 100676 | Lactococcus lactis subsp. cremoris | NBRC |
| JCM 1180 | Lactococcus lactis subsp. hordniae | JCM |
| JCM 11040 | Lactococcus lactis subsp. hordniae | JCM |
| JCM 1158 | Lactococcus lactis subsp. lactis | JCM |
| JCM 5805 | Lactococcus lactis subsp. lactis | JCM |
| JCM 12650 | Lactococcus lactis subsp. lactis | JCM |
| JCM 20101 | Lactococcus lactis subsp. lactis | JCM |
| JCM 20128 | Lactococcus lactis subsp. lactis | JCM |
| JCM 20312 | Lactococcus lactis subsp. lactis | JCM |
| JCM 20399 | Lactococcus lactis subsp. lactis | JCM |
| NBRC 12007 | Lactococcus lactis subsp. lactis | NBRC |
| NRIC 1147 | Lactococcus lactis subsp. lactis | NRIC |
| NRIC 1148 | Lactococcus lactis subsp. lactis | NRIC |
| NRIC 1150 | Lactococcus lactis subsp. lactis | NRIC |
| NBRC 12455 | Leuconostoc lactis | NBRC |
| NRIC 328 | Leuconostoc lactis | NRIC |
| NRIC 1540 | Leuconostoc lactis | NRIC |
| NRIC 1575 | Leuconostoc lactis | NRIC |
| JCM 6124 | Leuconostoc mesenteroides | JCM |
| NBRC 100496 | Leuconostoc mesenteroides | NBRC |
| JCM 5886 | Pediococcus damnosus | JCM |
| JCM 2026 | Pediococcus pentosaceus | JCM |
| JCM 5885 | Pediococcus pentosaceus | JCM |
| JCM 5890 | Pediococcus pentosaceus | JCM |
| JCM 20314 | Pediococcus pentosaceus | JCM |
| JCM 20459 | Pediococcus pentosaceus | JCM |
| JCM 20026 | Streptococcus thermophilus | JCM |
| ST-21 | Streptococcus thermophilus | DANISCO |
| TA40 | Streptococcus thermophilus | DANISCO |
| TA45 | Streptococcus thermophilus | DANISCO |

Fig. 2A

|  | Rod-shaped bacteria | Spherical-shaped bacteria |
|---|---|---|
| 50 pg/ml < IFN-α | 0 / 90 (0.00%) | 13 / 35 (34.29%) |

Fig. 2B

|            | Rod-shaped bacteria | Spherical-shaped bacteria |
|---|---|---|
| 100 pg/ml < IFN-α | 0 / 90 (0.00%) | 3 / 35 (8.57%) |

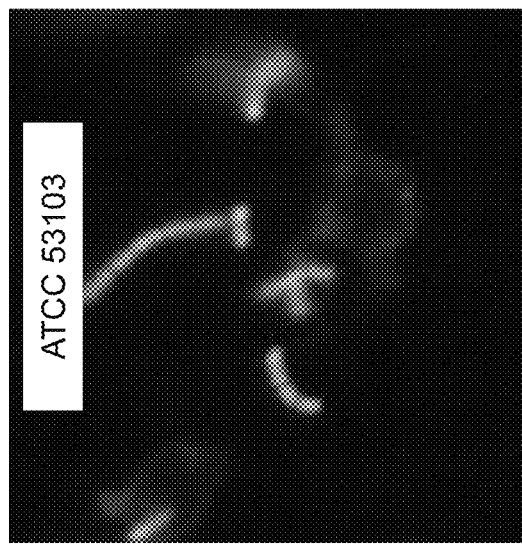
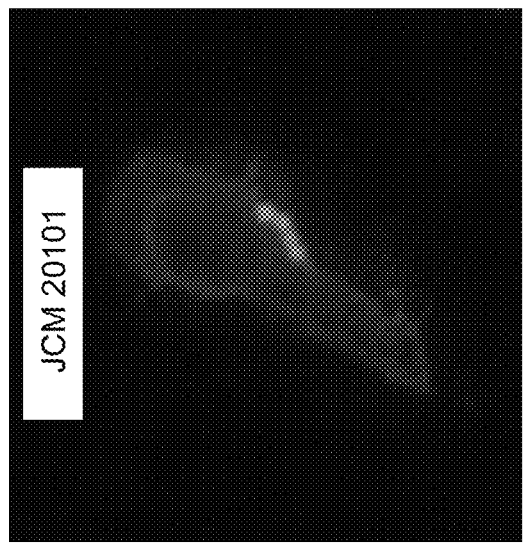
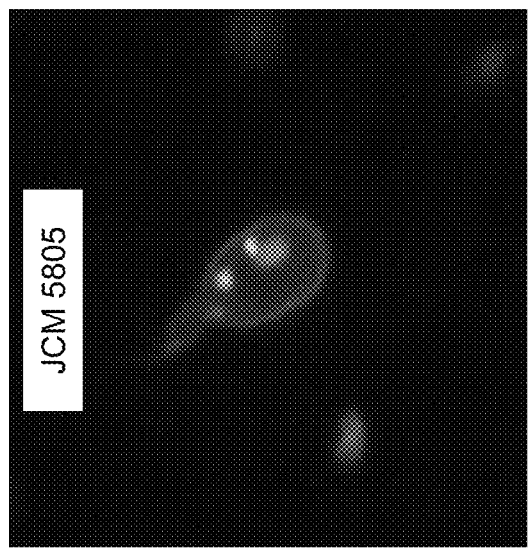

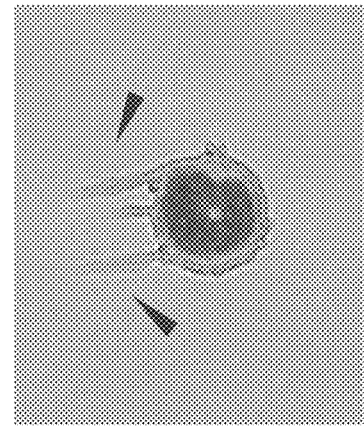
Fig. 8B JCM 5805
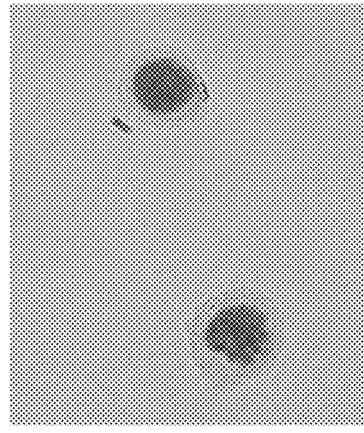
Fig. 8D ATCC 53103
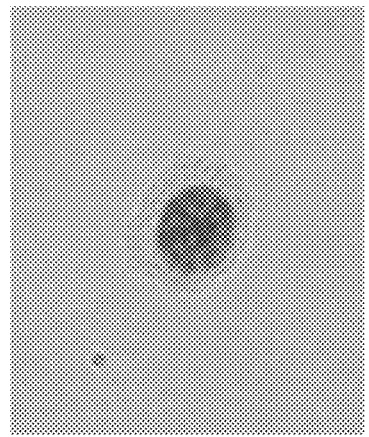
Fig. 8A ctrl
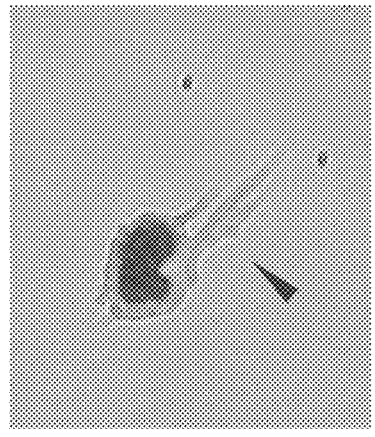
Fig. 8C JCM 20101

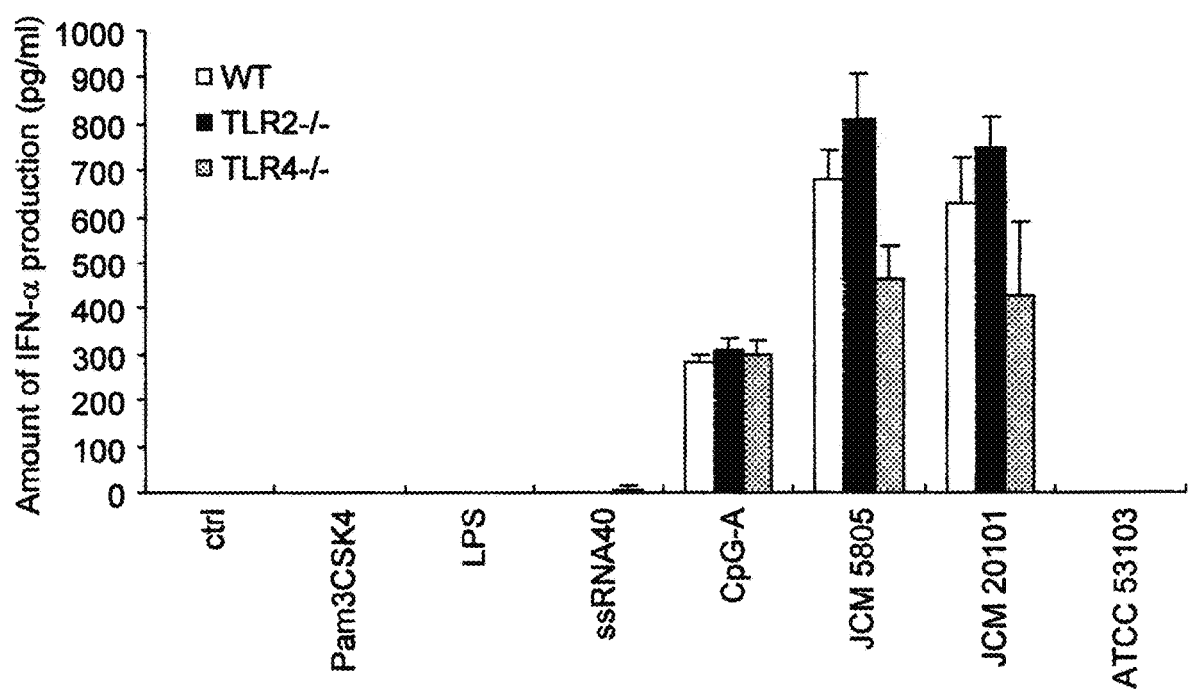

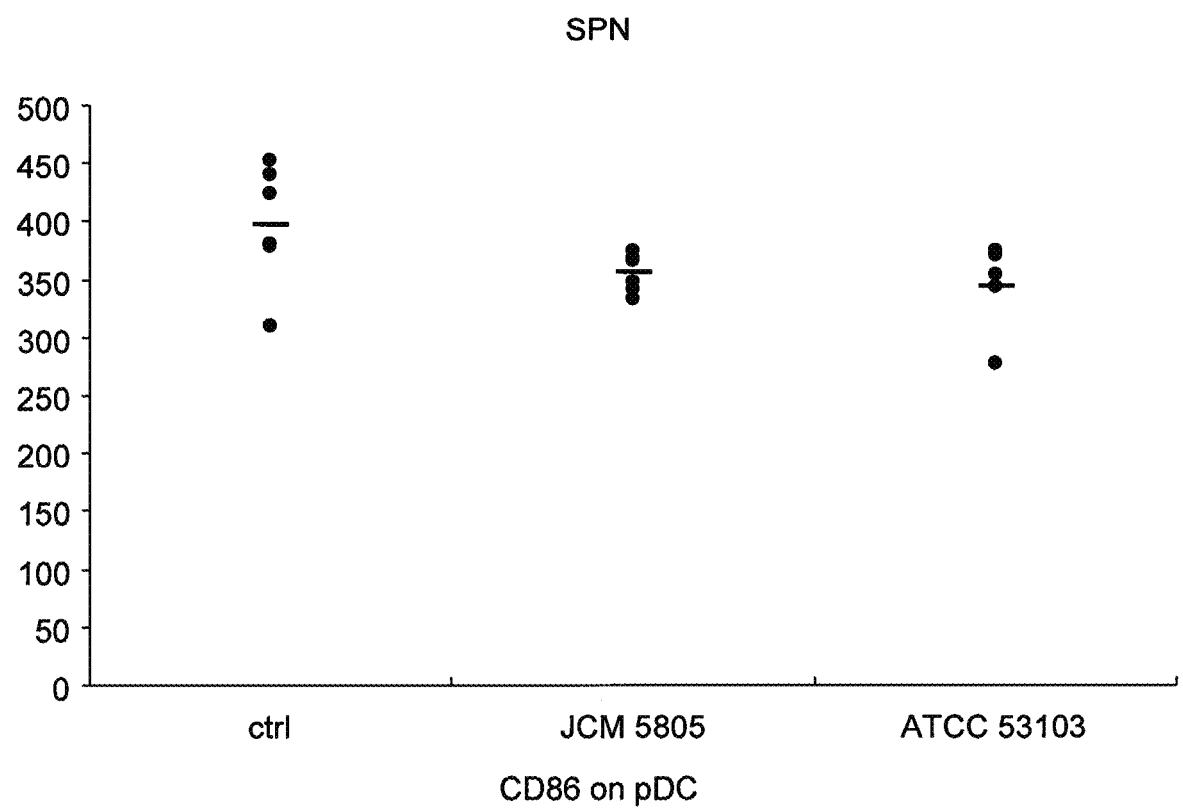

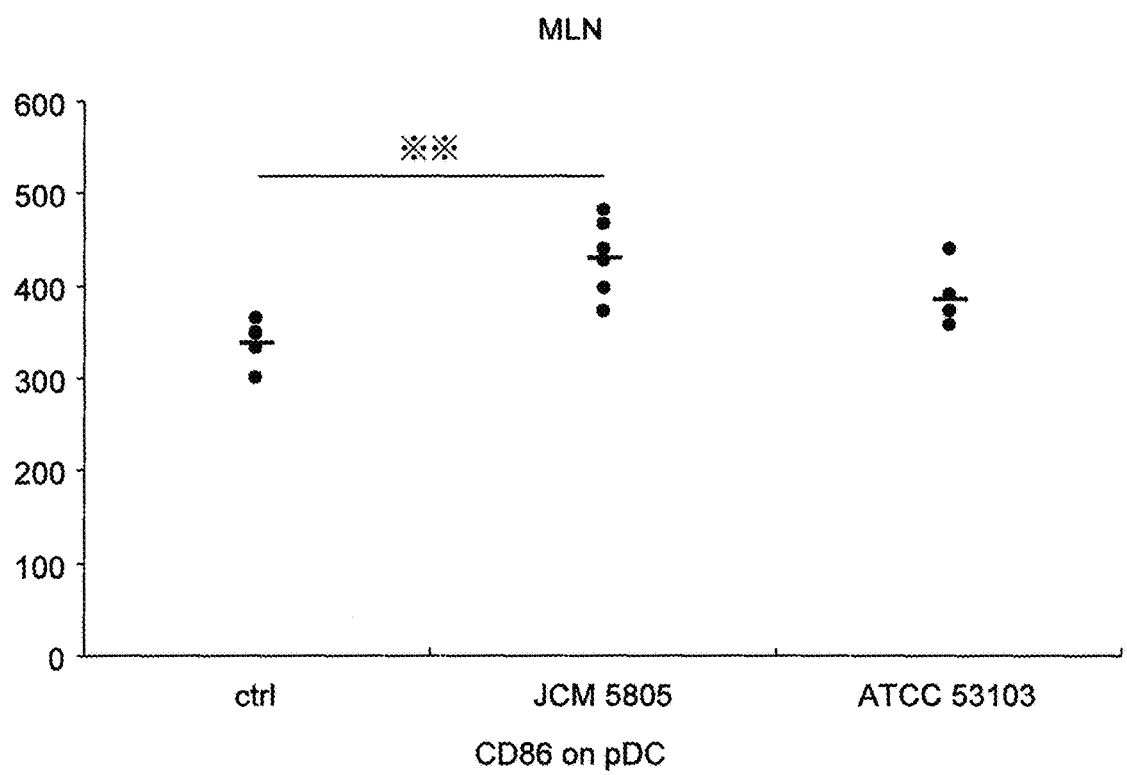

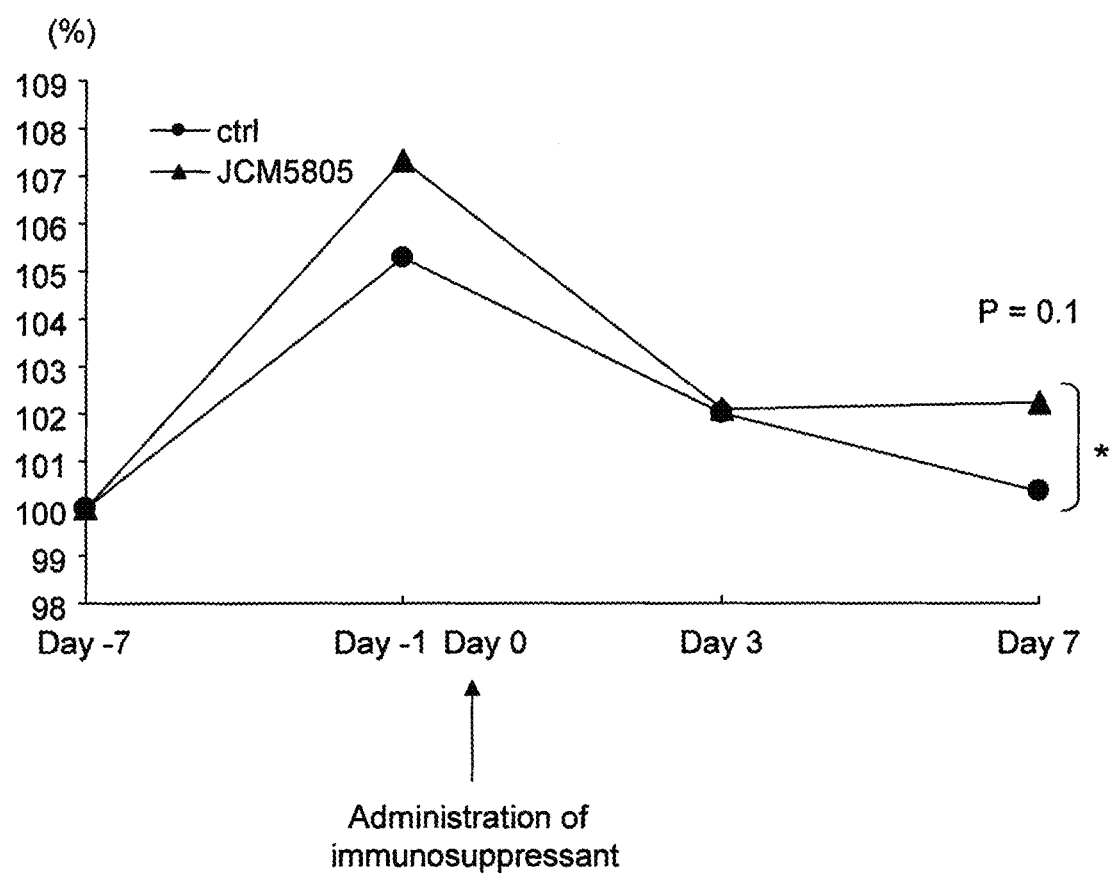

※※ : P<0.01 Mann-Whitney U-test with Bonferroni correction

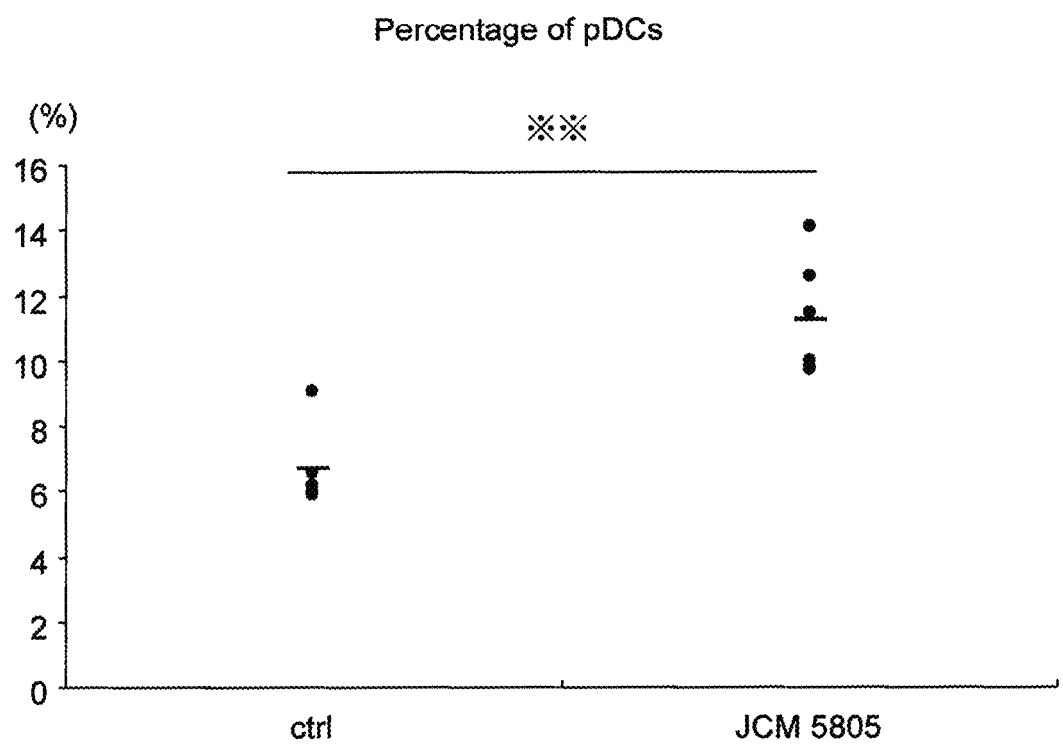

\# : p<0.05 vs. Placebo

\# : p<0.05 vs. Placebo

: $p<0.01$ by paired t-test

Fig. 23

|  | Score average | 1: No symptom | With symptom > 1 | $X^2$ square test (p value) |
|---|---|---|---|---|
| Week 1 | JCM5805 | 90 | 43 | 0.601 |
| | Placebo | 84 | 46 | |
| Week 2 | JCM5805 | 105 | 27 | 0.125 |
| | Placebo | 95 | 38 | |
| Week 3 | JCM5805 | 93 | 38 | 0.220 |
| | Placebo | 85 | 48 | |
| Week 4 | JCM5805 | 100 | 33 | 0.004 |
| | Placebo | 78 | 55 | |

AGENT FOR INDUCING INTERFERON PRODUCTION CONTAINING LACTIC ACID BACTERIA

CROSS-REFERENCE TO RELATED APPLICATIONS

This application is a Divisional of U.S. application Ser. No. 16/290,581, filed Mar. 1, 2019, now U.S. Pat. No. 11,224,623, which is a Divisional of U.S. application Ser. No. 15/367,649, filed Dec. 2, 2016, now U.S. Pat. No. 10,220,060, which is a Divisional of U.S. application Ser. No. 14/263,306, filed Apr. 28, 2014, now U.S. Pat. No. 9,549,956, which is a Continuation of U.S. application Ser. No. 13/977,435, now abandoned, which is the U.S. national phase of PCT/JP2011/080359, filed Dec. 28, 2011, which was published on Jul. 5, 2012, as WO 2012/091081, which claims the benefit of JP Application No. 2010-293810, filed Dec. 28, 2010, the entire contents of which are incorporated herein by reference.

TECHNICAL FIELD

The present invention relates to an agent for inducing interferon production containing lactic acid bacteria and a pharmaceutical product and a food or drink product containing the agent for inducing interferon production.

BACKGROUND ART

Bacteria, including lactic acid bacteria, are recognized and englobed by a group of immunocytes referred to as the innate immune system, and they cause physiological reactions, such as cytokine or chemokine production, changes in gene expression, and epigenetic gene modification. Cells of the innate immune system can be roughly classified as macrophages, natural killer (NK) cells, and dendritic cells. In contrast to the long-term antigen-specific reactions of the acquired immune system, the reactions of the innate immune system are short-lasting, non-antigen-specific, inclusive reactions. The innate immune system plays a key role in primary responses against infection with bacteria or viruses, and, in particular, dendritic cells are potent and critical constitutive cells. Dendritic cells are highly flexible, a great number of different subspecies thereof exist, and these cells can be roughly classified into myeloid dendritic cells (mDCs), CD8+ dendritic cells (CD8+ DCs), and plasmacytoid dendritic cells (pDCs). mDCs mainly release inflammatory cytokines, such as interleukin-12 (IL-12) and tumor necrosis factor-α (TNF-α), upon infection with bacteria and induce activation of helper T cells (CD4+ T cells). CD8+ DCs are high-power cells producing IL-12, which play a key role in induction of cytotoxic T lymphocytes (CTLs) upon virus infection or cross-priming of cancer antigens. pDCs are major cells producing type I interferon (IFN) exhibiting growth-inhibiting activity against viruses in vivo, and they play a critical role in antiviral biophylaxis. Representative examples of type I interferon include IFN-α and IFN-β. In order to induce such substances, it is necessary to stimulate Toll-like receptors (TLRs), in particular, endosomal TLRs, such as TLR3, TLR7, or TLR9. In general, viral double-stranded RNA, viral single-stranded RNA or an antiviral agent (imidazoquinoline), and non-methylated CpG DNA comprising cytosine and guanine joined by a phosphodiester bond are known as a TLR3 ligand, a TLR7 ligand, and a TLR9 ligand, respectively. Thus, nucleic acids of bacteria or viruses are known to serve as ligands in the induction of type I interferon production. IFN-α has been put into practical use as a therapeutic agent for hepatitis B, hepatitis C, chronic myeloid leukemia, multiple myeloma, renal cancer, and other diseases, and IFN-β has been put into practical use as a therapeutic agent for multiple sclerosis, in addition to hepatitis B and hepatitis C. Accordingly, pDC is considered to be the most important cell from the viewpoint of biophylaxis, and antiviral prophylaxis, in particular. IFN-γ is cytokine that is classified as type II interferon, and it is mainly produced by NK or Th1 cells, although antiviral effects thereof are weak. Accordingly, a main function thereof is considered to be enhancement of antiviral effects of IFN-α and IFN-β. In addition, the most recently discovered IFN-λ, is classified as type III interferon, such a cytokine has drawn attention recently because of its potent antiviral effects verified in recent years. IFN-λ, is produced mainly by pDCs in an organism, as with the case of type I IFN.

In addition to viruses, a certain bacteria are known to activate pDC or produce IFN-α. As bacteria that are verified to activate pDC, one of the food-poinsoning bacteria, *Staphylococcus aureus* has been reported. As bacteria that enhance IFN-α production in the blood, pathogenic bacteria, such as *Chlamydia, Salmonella*, Mycobacteria, and *Listeria*, are known. While some lactic acid bacteria have been reported to enhance IFN-α production (see Non-Patent Documents 1 and 2), the correlation thereof with pDC remains unknown, and screening has never been conducted using the capacity for IFN-α production or pDC activation as the indicator. Also, lactic acid bacteria have been reported to enhance IFN-β production (see Patent Documents 1 and 2 and Non-Patent Document 3) and to enhance IFN-γ production (see Patent Document 3); however, the correlation thereof with pDC also remains unknown. While it has been reported that IFN-λ, has antiviral activity (see Non-Patent Documents 4 and 5) and IFN-λ, is mainly produced by pDCs (Non-Patent Document 6), the correlation of IFN-λ, with lactic acid bacteria remains unknown.

PRIOR ART DOCUMENTS

Patent Documents

Patent Document 1: JP Patent Publication (Saihyo) No. 2009-005123 A
Patent Document 2: JP Patent Publication (Saihyo) No. 2009-005124 A
Patent Document 3: JP Patent Publication (Kokai) No. 2006-028047 A
Patent Document 4: JP Patent Publication (Kokai) No. 2001-46020 A
Patent Document 5: JP Patent Publication (Kokai) No. 2000-262247 A

Non-Patent Documents

Non-Patent Document 1: Yuichiro Fukui, Nobuhiro Yajima: Abstracts for the Annual Meeting of the Japanese Association for Food Immunology, 2006 (Oct. 23 to 24, 2006)
Non-Patent Document 2: "Shokuhin to Kaihatsu (Food Processing and Ingredients)," Vol. 42, NO. 5, 2007, pp. 85-87
Non-Patent Document 3: Tadaomi Kawashima, Ikuko Nishimura: Abstracts for the Annual Meeting of the Japan Society for Lactic Acid Bacteria, 2010 (Jul. 26 to 27, 2010)
Non-Patent Document 4: Nature Immunology, 4: 69-77, 2002

Non-Patent Document 5: Gastroenterology, 131: 1887-1898, 2006
Non-Patent Document 6: Blood, 115: 4185-90, 2010
Non-Patent Document 7: The Journal of Immunology, 186: 1685-1693, 2011
Non-Patent Document 8: Journal of Leukocyte Biology 83: 296-304, 2008

SUMMARY OF THE INVENTION

Object to be Attained by the Invention

The present invention is intended to provide an IFN inducer capable of inducing IFN production comprising, as an active ingredient, lactic acid bacteria, an immunopotentiating agent or prophylactic agent against virus infection comprising such inducer, and a food or drink product comprising such inducer and having IFN inducing activity, immunopotentiating activity, or prophylactic activity against virus infection.

Means for Attaining the Object

The present inventors constructed an assay system involving the use of pDC activation as the indicator and selected lactic acid bacteria that would potentiate the prophylactic activity against virus infection through ingestion thereof.

As a result, they discovered that some spherical-shaped lactic acid bacteria would activate pDCs and induce interferon production from such pDCs. They further discovered that some lactic acid bacteria would be capable of exerting the effects in an organism even they were orally administered. The present inventors discovered that the lactic acid bacteria could be used as agents for inducing IFN production, and such bacteria could also be used for prophylaxis against virus infection because of the immunopotentiating activity of an organism. This has led to the completion of the present invention.

Specifically, the present invention is as follows.

[1] An agent for inducing IFN production comprising, as an active ingredient, lactic acid bacteria capable of activating plasmacytoid dendritic cells (pDCs) and inducing IFN production or a cultured product thereof.

[2] The agent for inducing IFN production according to [1], wherein the processed product of lactic acid bacteria is a fraction containing nucleic acids.

[3] The agent for inducing IFN production according to [1] or [2], wherein IFN is type I IFN or type III IFN.

[4] The agent for inducing IFN production according to any of [1] to [3], wherein IFN is at least one member selected from the group consisting of IFN-α, IFN-β, and IFN-λ.

[5] The agent for inducing IFN production according to any of [1] to [4], wherein, when the agent is orally administered, the lactic acid bacteria capable of activating plasmacytoid dendritic cells (pDCs) and inducing IFN production are highly tolerant to the gastric juice or intestinal juice and are capable of reaching the intestinal canal alive.

[6] The agent for inducing IFN production according to [5], wherein the lactic acid bacteria capable of activating plasmacytoid dendritic cells (pDCs) and inducing IFN production are *Lactococcus lactis* subsp. *lactis* JCM5805.

[7] An immunopotentiating agent comprising the agent for inducing IFN production according to any of [1] to [6].

[8] An agent for prevention or treatment of virus infection comprising the agent for inducing IFN production according to any of [1] to [6].

[9] The immunopotentiating agent according to [7], which is an oral preparation.

[10] The agent for prevention or treatment of virus infection according to [8], which is an oral preparation.

[11] A food or drink product comprising the agent for inducing IFN production according to any of [1] to [6].

[12] The food or drink product according to [11], which is cheese or yogurt.

[13] A method of screening for lactic acid bacteria capable of activating plasmacytoid dendritic cells (pDCs) and inducing IFN production comprising culturing the lactic acid bacteria with bone marrow cells and detecting activation of plasmacytoid dendritic cells (pDCs) and induction of IFN production, wherein, when plasmacytoid dendritic cells (pDCs) are activated and IFN production is induced, the lactic acid bacteria are determined to be capable of activating plasmacytoid dendritic cells (pDCs) and inducing IFN production.

[14] A host microorganism for a recombinant vaccine comprising the agent for inducing IFN production according to any of [1] to [6].

This description includes part or all of the content as disclosed in the description and/or drawings of Japanese Patent Application No. 2010-293810, which is a priority document of the present application.

Effects of the Invention

As described in the examples of the present application, the agent for inducing IFN production comprising, as an active ingredient, the particular lactic acid bacteria of the present invention is capable of activating pDC and inducing production of interferon, such as IFN-α, in vitro and in vivo. As a result of induction of interferon production in vivo, immune responses of an organism are potentiated, the organism is protected from infection with viruses or the like, and virus infections could be treated. The IFN inducer comprising, as an active ingredient, lactic acid bacteria described above can be used as a pharmaceutical product for potentiating immune responses for prevention or treatment of virus infection. Further, such inducer can be used as a component of a food or drink product for potentiating immune responses useful for prevention of virus infection.

BRIEF DESCRIPTION OF THE DRAWINGS

FIG. 1A shows a list of the tested lactic acid bacteria (Part 1).

FIG. 1B shows a list of the tested lactic acid bacteria (Part 2).

FIG. 1C shows a list of the tested lactic acid bacteria (Part 3).

FIG. 2A shows the number and ratio of lactic acid bacteria producing 50 pg/ml or more IFN-α, when compared rod-shaped bacteria with spherical-shaped bacteria.

FIG. 2B shows the number and ratio of lactic acid bacteria producing 100 pg/ml or more IFN-α, when compared rod-shaped bacteria with spherical-shaped bacteria.

FIGS. 4A-4C show differences in lactic acid bacteria recognition (uptake) of pDCs. FIG. 4A, FIG. 4B, and FIG. 4C show *Lactococcus lactis* JCM5805, *Lactococcus lactis* JCM21101, and *Lactobacillus rhamnosus* ATCC53103, respectively.

FIGS. 8A-8D show pDC configurations when *Lactococcus lactis* JCM5805, *Lactococcus lactis* JCM20101, and *Lactobacillus rhamnosus* ATCC53103 are added to the pDC monoculture system. FIG. 8A shows the results concerning the control (to which no lactic acid bacteria were added), FIG. 8B shows pDCs when *Lactococcus lactis* JCM5805 is added, FIG. 8C shows pDCs when *Lactococcus lactis* JCM20101 is added, and FIG. 8D shows pDCs when *Lactobacillus rhamnosus* ATCC53103 is added.

FIG. 9A shows the amounts of IFN-α production when *Lactococcus lactis* JCM5805, *Lactococcus lactis* JCM20101, and *Lactobacillus rhamnosus* ATCC53103 are added to the pDC/mDC cells generated from TLR2 and TLR4 knockout mice.

FIG. 13C shows changes in CD86 levels in pDCs of the spleen of healthy mice that had ingested *Lactococcus lactis* JCM5805.

FIG. 13D shows changes in CD86 levels in pDCs of the mesenteric lymph nodes of healthy mice that had ingested *Lactococcus lactis* JCM5805.

FIG. 15A shows the effects of ingestion of *Lactococcus lactis* JCM5805 using the immunosuppression models with reference to changes in the body weights of mouse models.

FIG. 16C shows the percentage of pDCs in the immunosuppression mouse models that had ingested *Lactococcus lactis* JCM5805.

FIG. 23 shows the results of comparison between the group subjected to ingestion of yogurt containing *Lactococcus lactis* JCM5805 and the placebo group regarding the development of cold symptoms during the period of test product ingestion examined every week.

EMBODIMENTS FOR CARRYING OUT THE INVENTION

Figure 3B:
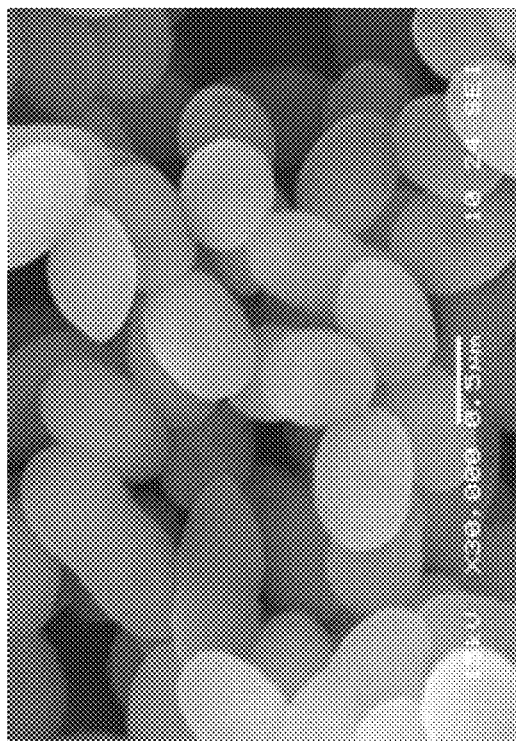
FIGS. 3A and 3B show electron microscopy of *Lactococcus lactis* JCM5805 (FIG. 3A) and *Lactococcus lactis* JCM20101 (FIG. 3B).

Hereafter, the present invention is described in detail.

The present invention relates to an agent for inducing IFN production comprising, as an active ingredient, lactic acid bacteria. The term "inducing (or variations thereof) IFN production" used herein refers to induction of IFN production in vitro and in vivo.

Lactic acid bacteria that can be used as the agent for inducing IFN production in the present invention are capable of activating plasmacytoid dendritic cells (pDCs) and promoting IFN production of pDCs. Further, lactic acid bacteria that can be used as the agent for inducing IFN production in the present invention are capable of promoting expression of activation markers, such as CD80, CD86, and MEW class II, in pDCs. Whether or not candidate lactic acid bacteria have such properties may be determined by, for example, culturing candidate lactic acid bacteria in the presence of bone marrow cells generated from mammalians, such as mice, and detecting the occurrence of pDC activation and induction of production of IFN, such as IFNα and IFNβ. IFN may be assayed by measuring the IFN concentration in a culture solution via, for example, ELISA. Lactic acid bacteria that can be used as an agent for inducing IFN production in the present invention has property as described below. For example, mouse bone marrow cells from which erythrocytes have been removed are suspended to a concentration of $5\times10^5$ cells/ml in RPMI medium (SIGMA) containing 10% FCS and 2 μM β-mercaptoethanol, Flt-3L is added as a pDC inducing cytokine to a final concentration of 100 ng/ml to the resulting cell suspension, the resultant is cultured in a $CO_2$ incubator at 37° C. in the presence of 5% $CO_2$, lactic acid bacteria are added thereto 7 days later at 10 μg/ml, the culture supernatant is collected 48 hours later, the IFN-α concentration in the culture supernatant is assayed via ELISA with the use of the IFN-α assay kit (PBL), and the determined IFN-α concentration is preferably 50 pg/ml or higher, and more preferably 100 pg/ml or higher.

Examples of preferable lactic acid bacteria that can activate plasmacytoid dendritic cells (pDCs) and promote IFN production of pDCs include spherical-shaped lactic acid bacteria. Specifically, spherical-shaped lactic acid bacteria that belong to the genera *Lactococcus, Leuconostoc, Pediococcus*, and *Streptococcus* are more preferable. Particularly preferable strains are *Lactococcus garvieae, Lactococcus lactis* subsp. *cremoris, Lactococcus lactis* subsp. *lactis, Lactococcus lactis* subsp. *hordniae, Leuconostoc lactis, Pediococcus damnosus*, and *Streptococcus* thermophiles.

Specific examples of such lactic acid bacteria include *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, and *Streptococcus thermophilus* TA-45. Among these strains, the capacity for inducing IFN-α production of *Lactococcus lactis* subsp. *lactis* JCM5805 and that of *Lactococcus lactis* subsp. *lactis* JCM20101 are particularly high. Thus, use of *Lactococcus lactis* JCM5805 is particularly preferable.

Lactic acid bacteria that can be used as the agent for inducing IFN production in the present invention preferably exert activity of IFN induction in an organism when such bacteria are ingested orally. Such lactic acid bacteria are highly tolerant to the gastric or intestinal juice. For example, such lactic acid bacteria have high-level tolerance to acids and are capable of reaching the intestinal canal alive. When *Lactococcus lactis* JCM5805 described above is orally ingested, it is capable of exerting a significant degree of activity for inducing IFN production in an organism.

Figure 17:
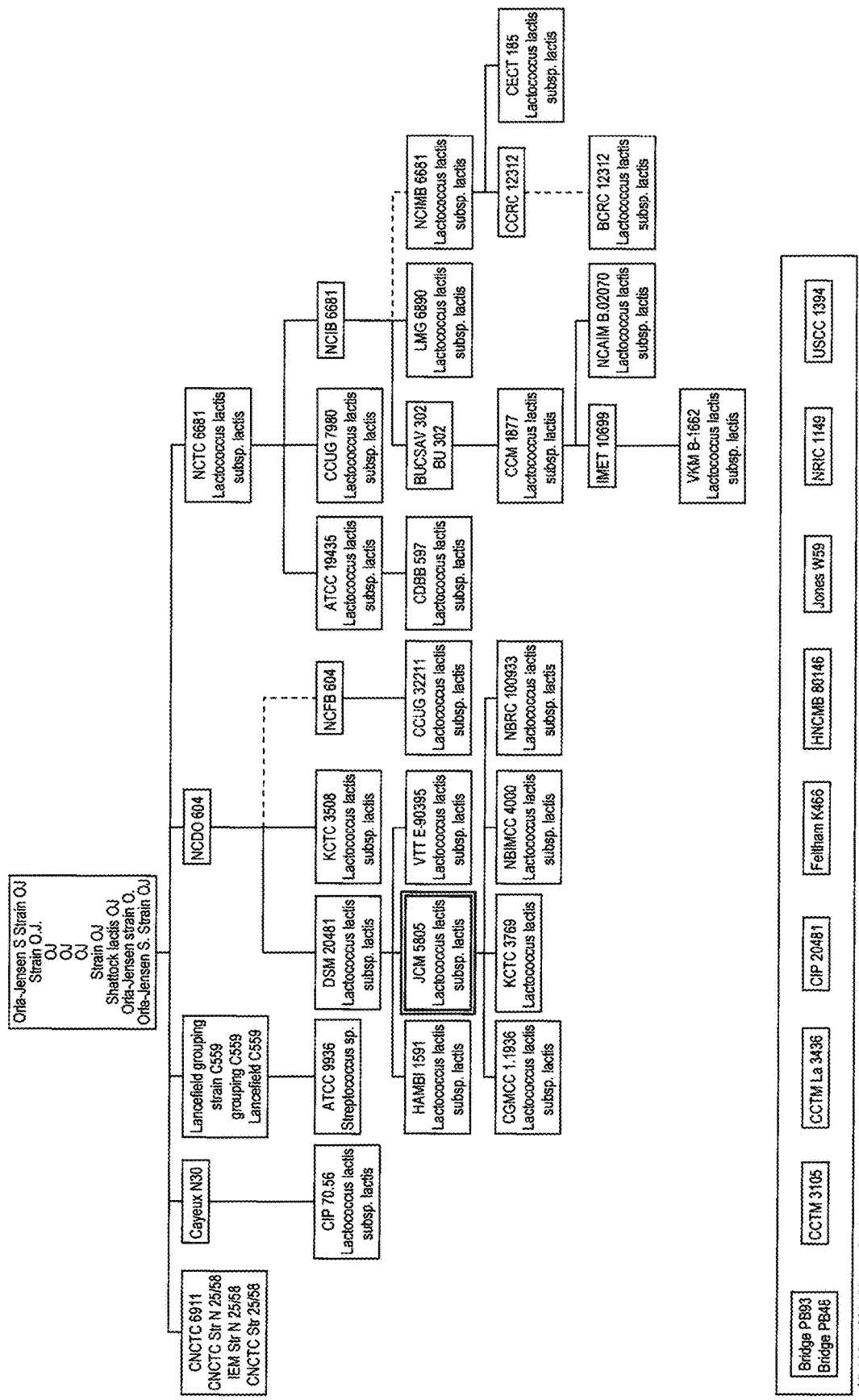
FIG. 17 shows *Lactococcus lactis* JCM5805 and a strain equivalent thereto (a strain derived from *Lactococcus lactis* JCM5805 and a strain from which *Lactococcus lactis* JCM5805 is derived). As used herein. "*Lactococcus lactis* JCM5805" refers to *Lactococcus lactis* subsp. *lactis* (Lister) Schleifer et al., deposited under international accession number JCM5805 with the Japan Collection of Microorganisms of the RIKEN BioResource Center (3-1-1 Koyadai, Tsukuba-shi, Ibaraki, Japan)) in 1986.

The lactic acid bacteria described above can be obtained from the RIKEN BioResource Center (3-1-1 Koyadai, Tsukuba-shi, Ibaraki, Japan), the Biological Resource Center (NBRC) at the National Institute of Technology and Evaluation (http://www.nbrc.nite.go.jp), the Culture Collection Center, Tokyo University of Agriculture (http://nodai-web.university.jp/nric/), and DANISCO. In addition, bacterial strains equivalent to the strains, such as *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, or *Streptococcus thermophilus* TA-45, can also be used. Equivalent strains include strains derived from the bacterial strains mentioned above, the bacterial strains from which the strains mentioned above are derived, or offspring strains of such bacterial strains. Equivalent strains may be conserved in other institutions for culture collection. FIG. 17 shows bacterial strains derived from *Lactococcus lactis* JCM5805 and bacterial strains from which *Lactococcus lactis* JCM5805 is derived. Bacterial strains equivalent to *Lactococcus lactis* JCM5805 shown in FIG. 17 can also be used as active ingredients of the agent for inducing IFN production of the present invention. The term "*Lactococcus lactis* JCM5805" used herein also refers to such equivalent strains. Other lactic acid bacteria that can be used as the agent for inducing IFN production of the present invention can be obtained from, for example, the RIKEN BioResource Center, American type culture collection (U.S.A.), the Institute for Fermentation (2-17-85 Jusohonmachi, Yodogawa Ward, Osaka, Osaka Prefecture, Japan), or the Culture Collection Center, Tokyo University of Agriculture (1-1-1, Sakuragaoka, Setagaya, Tokyo, Japan).

The agent for inducing IFN production of the present invention can induce any of type I interferon (type I IFN), type II interferon (type II IFN), or type III interferon (type III IFN). Type I IFN is a cytokine that is effective against virus infection, and examples thereof include IFN-α1, IFN-α2, IFN-α4, IFN-α5, IFN-α6, IFN-α7, IFN-α8, IFN-α10, IFN-α13, IFN-α14, IFN-α16, IFN-α17, IFN-α21, and IFN-β. An example of type II IFN is IFN-γ, and an example of type III IFN is IFN-λ. The agent for inducing IFN production of the present invention has activity of inducing production of type I IFN, in particular. The agent for inducing IFN production of the present invention activates plasmacytoid dendritic cells (pDCs). When a plasmacytoid dendritic cell is activated, a cell process, which is characteristic of the activated dendritic cell, appears, and type I IFN and type III IFN are produced. At this time, lactic acid bacteria, which are active ingredients of the agent for inducing IFN production of the present invention, are incorporated into pDCs. The agent for inducing IFN production of the present invention has the high capacity for inducing production of type I IFN and type III IFN, and the capacity for inducing production of IFN-α, which is type I IFN, is particularly high. The agent for inducing IFN production of the present invention is also capable of inducing production of type II IFN, such as IFN-γ, from NK cells or Th1 cells. Immune activity of an organism is enhanced via induction of IFN production. However, lactic acid bacteria, which are active ingredients of the agent for inducing IFN production of the present invention, are capable of inducing the expression of PDL-1. PDL-1 is a programmed death ligand-1 (PD-1), and PDL-1 binds to PD-1 and induces regulatory T cells, so that PDL-1 can prevent an immune system from being excessively activated and suppress the autoimmune reactions. Specifically, the agent for inducing IFN production of the present invention is not only capable of inducing IFN production and activating the immune functions of an organism but also capable of suppressing excessive immune reactions and maintaining the balanced immune reactions in the organism.

The agent for inducing IFN production of the present invention can simultaneously induce production of type I IFN and type III IFN. Specifically, production of IFN-α, IFN-β, and IFN-λ, can be induced simultaneously.

The agent for inducing IFN production of the present invention promotes expression of CD80, CD86, and MHC class II in pDCs. TLR9 is involved in the induction of IFN production as a receptor.

The agent for inducing IFN production of the present invention contains a culture product of the lactic acid bacteria above. The term "culture product" refers to live bacteria, killed bacteria, fragmented live or killed bacteria, lyophilized live or killed bacteria, or a fragmented product, culture solution, or culture extract of such lyophilized bacteria. The term also refers to part of lactic acid bacteria or treated lactic acid bacteria. Examples of treated lactic acid bacteria include products resulting from enzyme or thermal treatment of lactic acid bacteria and products recovered through ethanol precipitation of the products of enzyme or thermal treatment. Further, DNA or RNA of the above lactic acid bacteria is within the scope of the culture product of lactic acid bacteria. DNA or RNA of the above lactic acid bacteria is considered to be capable of activating pDCs and inducing IFN production.

Lactic acid bacteria can be cultured in accordance with a conventional technique using conventional media. Examples of media that can be used include MRS, GAM, and LM17 media, and inorganic salts, vitamins, amino acids, antibiotics, sera, or other substances may be added thereto, according to need. Culture may be carried out at 25° C. to 40° C. for several hours to several days.

After culture, lactic acid bacteria are harvested via centrifugation, filtration, or other means. When used in the form of killed bacteria, bacteria may be sterilized and inactivated with the use of an autoclave, for example.

Activity for inducing IFN production of lactic acid bacteria that can be used as active ingredients of the agent for inducing IFN production of the present invention can be assayed by culturing candidate bacteria, culturing IFN-producing cells in the presence of the culture product thereof, and detecting an increase in the amount of IFN produced by the IFN-producing cells. Typically, lyophilized bacteria are used. The weight of bacteria in the lyophilization product is adjusted to 0.1 to 5 mg/ml, and the lyophilization product is then cultured with, for example, bone marrow cells. Origins of bone marrow cells are not particularly limited, and bone marrow cells derived from humans or bone marrow cells derived from non-human animals such as mice can be used. When pDCs are activated and IFN production is induced in the bone marrow cells, the lactic acid bacteria can be determined to be usable as active ingredients of the agent for inducing IFN production of the present invention. Activation of pDCs may be detected by, for example, assaying pDC activation markers, and examples of activation markers include CD80, CD86, and MEW class II. Such activation markers can be assayed via cell staining or flow cytometry using antibodies reacting with such markers. Examples of IFN include type I IFNs such as IFN-α and IFN-β, type II IFNs such as IFN-γ, and type III IFN such as IFN-λ. Among them, type I IFN and type III IFN are preferable, type I IFN is more preferable, and IFN-α is further preferable. Induction of IFN production may be assayed by determining the amount of IFN in a medium in the culture system via, for example, ELISA.

The present invention includes a method for screening for lactic acid bacteria having activity of inducing IFN production and usable as active ingredients of the agent for inducing IFN production of the present invention.

The agent for inducing IFN production of the present invention can be used in the form of a pharmaceutical product that induces IFN production and enhances immune activity of an organism. Specifically, the agent for inducing IFN production can be used in the form of an immunopotentiating agent or immunostimulator. Such pharmaceutical products can be used for preventive or therapeutic agents for diseases, which are already known to be associated with type I IFN. Examples of such diseases include: cancer, including renal cancer, multiple myeloma, chronic myeloid leukemia, hairy cell leukemia, gliosarcoma, medulloblastoma, astroglioma, malignant melanoma, mycosis fungoides, and adult T cell leukemia; virus infection, including subacute sclerosing panencephalitis, HTLV-1 associated myelopathy, hepatitis B, and hepatitis C; infection with bacteria, such as *chlamydia* (sexually transmitted disease), Mycobacteriaceae (tuberculosis), listeriosis (ichorrhemia), *Staphylococcus* (food poisoning), and *Helicobacter* (gastritis); and autoimmune diseases including multiple sclerosis. The pharmaceutical product is particularly useful as a prophylactic or therapeutic agent for virus infection. Since the function of inhibiting differentiation of osteoblasts into osteoclasts is known as activity of type I IFN, it can be used as a preventive or therapeutic agent for osteoporosis.

An antigen associated with a particular disease may be expressed in spherical-shaped lactic acid bacteria, which is the IFN inducer of the present invention, via genetic engineering, and the resultant may be used as a vaccine. Since the cell wall of lactic acid bacteria can protect antigens from gastric acid, such bacterial strains expressing foreign antigens are particularly preferable as host organisms of oral vaccines. In general, vaccines are classified as live vaccines, inactivated whole particle vaccines, or split vaccines. However, live vaccines pose a risk of potentiating the virus virulence, inactivated whole particle vaccines may evoke side effects because of the presence of impurities, and split vaccines with the highest safety are problematic in terms of efficacy. In order to overcome such drawbacks, development of recombinant vaccines selectively expressing target antigens has been attempted. If the target antigens are expressed in the spherical-shaped lactic acid bacteria having the effects of IFN induction according to the present invention, effects of an adjuvant can also be achieved, and it is thus very useful.

Dosage forms of the agent for inducing IFN production of the present invention are not particularly limited. Examples include powder, granules, tablets, syrup, injection preparations, drops, powdered drugs, suppositories, suspensions, and ointments. The pharmaceutical product of the present invention may be administered orally or parenterally through intravenous injection, intramuscular injection, subcutaneous administration, rectal administration, or transdermal administration, with oral administration being preferable. The agent for inducing IFN production may contain an excipient, a disintegrator, a binder, a lubricant, a colorant, or the like. Examples of excipients include glucose, lactose, corn starch, and sorbit. Examples of disintegrators include starch, sodium alginate, powdered gelatin, calcium carbonate, calcium citrate, and dextrin. Examples of binders include dimethylcellulose, polyvinyl alcohol, polyvinyl ether, methylcellulose, ethylcellulose, gum Arabic, gelatin, hydroxypropyl cellulose, and polyvinyl pyrrolidone. Examples of lubricants include talc, magnesium stearate, polyethylene glycol, and hydrogenated vegetable oil. A dose can be adequately determined in accordance with the age, body weight, or sexuality of a patient, a type of disease, severity of symptoms, or other conditions. The agent may be administered once or several separate times per day, and a culture product may be administered in an amount equivalent to $1 \times 10^9$ to $1 \times 10^{12}$ cells in a single instance. Alternatively, a dose may be 1 to 1,000 mg of lactic acid bacteria.

The agent for inducing IFN production of the present invention can be incorporated into a food or drink product. Thus, the resulting food or drink product can be used for induction of IFN production, immunopotentiation, immunostimulation, prophylaxis against virus infection, or other purposes. Target food or drink products are not particularly limited, provided that active ingredients for induction of IFN production are not inhibited. Examples include milk, dairy products, beverage, seasonings, alcoholic beverage, agricultural products, processed forest products, confectioneries, breads, cereals, noodles, seafood products, processed livestock products, oils and fats, processed oils and fats, prepared frozen foods, retort foods, ready-to-eat foods, and food materials. Use of fermented dairy products, such as yogurt or cheese, and drinks containing lactic acid bacteria is particularly suitable. When used in the form of fermented food or drink products, given amounts of killed lactic acid bacteria having activity of inducing IFN production may be added to fermented food or drink products. Alternatively, such lactic acid bacteria may be used as starters to produce fermented food or drink products.

A fraction containing large quantities of nucleic acids of the lactic acid bacteria of the present invention can also be used as the agent for inducing IFN production. A nucleic acid may be DNA, RNA, or a mixture thereof, with DNA being preferable. Such fraction can be prepared by, for example, enzyme or thermal treatment (Patent Document 4) or recovery of a precipitate obtained with the aid of ethanol (Patent Document 5). In the present invention, such fraction is referred to as a processed product of lactic acid bacteria. With the use of such fraction, a more effective health food or drink product with enriched active ingredients can be provided.

Examples of the food or drink product of the present invention include a health food or drink product, a food or drink product for specified health use, a food or drink product with nutrient function claims, and a dietary supplement food or drink product. The term "food or drink product for specified health use" refers to a food or drink product that is to be ingested for specified healthcare objectives and has a labeling indicating that the objectives can be expected through ingestion thereof. Such food or drink product may be provided with a labeling indicating that, for example, enhancement of body's immune functions, stimulation of body's immune functions, lowering of susceptibility to colds, enhancement of tolerance to infection with viruses such as influenza virus, norovirus, or rotavirus, or cancer prevention.

EXAMPLES

The present invention is described in detail with reference to the following examples, although the present invention is not limited to these examples.

Example 1

Preparation of Test Lactic Acid Bacteria
<Experimental Method>
The lactic acid bacteria shown in FIG. 1A, FIG. 1B, and FIG. 1C were subjected to thermal treatment to prepare killed lactic acid bacteria. At the outset, the lactic acid bacteria mentioned above were purchased from microbial strain libraries in Japan and abroad. The lactic acid bacteria were obtained from the Japan Collection of Microorganisms (JCM) of the RIKEN BioResource Center, the Culture Collection Center of the Institute of Fermentation, Osaka (IFO), the NODAI Culture Collection Center (NRIC) of Tokyo University of Agriculture, American Type Culture Collection (ATCC, U.S.A.), and DANISCO. A total of 125 strains of 31 different species were obtained. Lactic acid bacteria were subjected to stationary culture in MRS, GAM, or LM17 medium at 30° C. or 37° C. for 24 to 48 hours. The strains were harvested, washed three times with sterile water, and then disinfected in an autoclave at 100° C. for 30 minutes. Thereafter, the strains were lyophilized, and the concentration was adjusted to 1 mg/ml with PBS (Takara Bio).

Example 2

Screening for Lactic Acid Bacteria Having Capacity for Inducing IFN-α Production
The capacity of the lactic acid bacteria prepared in Example 1 for inducing IFN-α production was evaluated with reference to pDC activation.
<Experimental Method>
Bone marrow cells were collected from the femoral bones of C57BL/6 mice in accordance with a conventional technique, and erythrocytes were removed therefrom. Subsequently, the collected bone marrow cells were suspended to a concentration of $5 \times 10^5$ cells/ml in RPMI medium (SIGMA) containing 10% FCS and 2 μM β-mercaptoethanol. Flt-3L (R&D Systems) was added as a pDC inducing cytokine to a final concentration of 100 ng/ml to the resulting cell suspension, and culture was conducted in a $CO_2$ incubator at 37° C. in the presence of 5% $CO_2$. Various types of lactic acid bacteria were added thereto 7 days later at 10 µg/ml, and the culture supernatant was collected 48 hours later. The culture supernatant was subjected to ELISA assays with the use of the IFN-α assay kit (PBL).

<Results>

FIG. 2 shows strains evaluated to be capable of producing 50 pg/ml or more IFN-α via ELISA. Among the 125 tested strains, activity was observed in only 13 strains (i.e., *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, and *Streptococcus thermophilus* TA-45). There were only 3 strains (i.e., *Lactococcus lactis* subsp. *lactis* NRIC1150, *Lactococcus lactis* subsp. *lactis* JCM5805, and *Lactococcus lactis* subsp. *lactis* JCM20101) that had been evaluated to be capable of producing 100 pg/ml or more IFN. Most bacteria did not have the capacity for inducing IFN-α production on pDCs. This indicates that such activity is not universal among various types of lactic acid bacteria.

The selected 3 strains inducing the production of IFN at a high level (i.e., 100 pg/ml or more IFN) were spherical-shaped bacteria classified as *Lactococcus lactis* subsp. *lactis*. As shown in FIG. 2A, further, the hit rate of spherical-shaped lactic acid bacteria is 34.29%, which is significantly higher than that of rod-shaped lactic acid bacteria (i.e., 0.00%). In the case of strains inducing the production of IFN at a high level shown in FIG. 2B, the hit rate of spherical-shaped lactic acid bacteria is 8.57%, which is also higher than that of rod-shaped lactic acid bacteria (i.e., 0.00%). This indicates that activity of stimulating pDCs to induce IFN-α production is characteristic of spherical-shaped lactic acid bacteria. While activity of directly stimulating pDCs by *Staphylococcus aureus* was reported, the capacity for pDC activation of ingestible bacteria that are harmless to humans was discovered for the first time.

The *Lactococcus lactis* JCM5805 and JCM20101 strains exhibiting the capacity for inducing IFN-α production at a particularly significant level and, as a negative control, the rod-shaped *Lactobacillus rhamnosus* ATCC53103 strain were subjected to the following analysis.

Figure 3A:
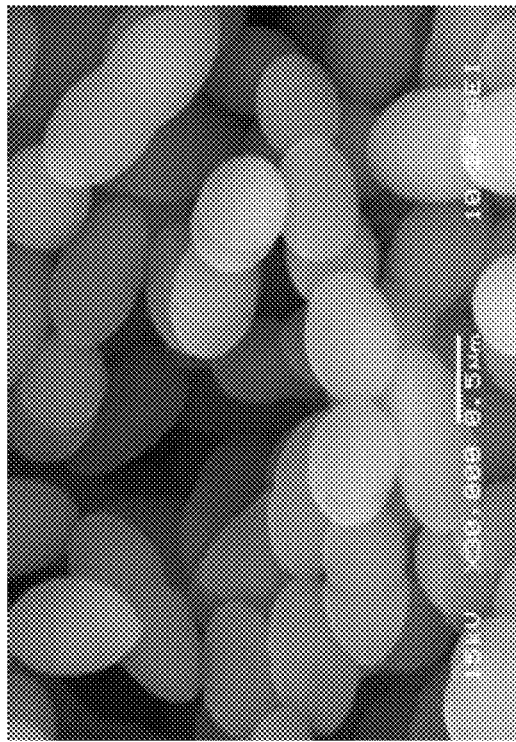
Figure 5A:
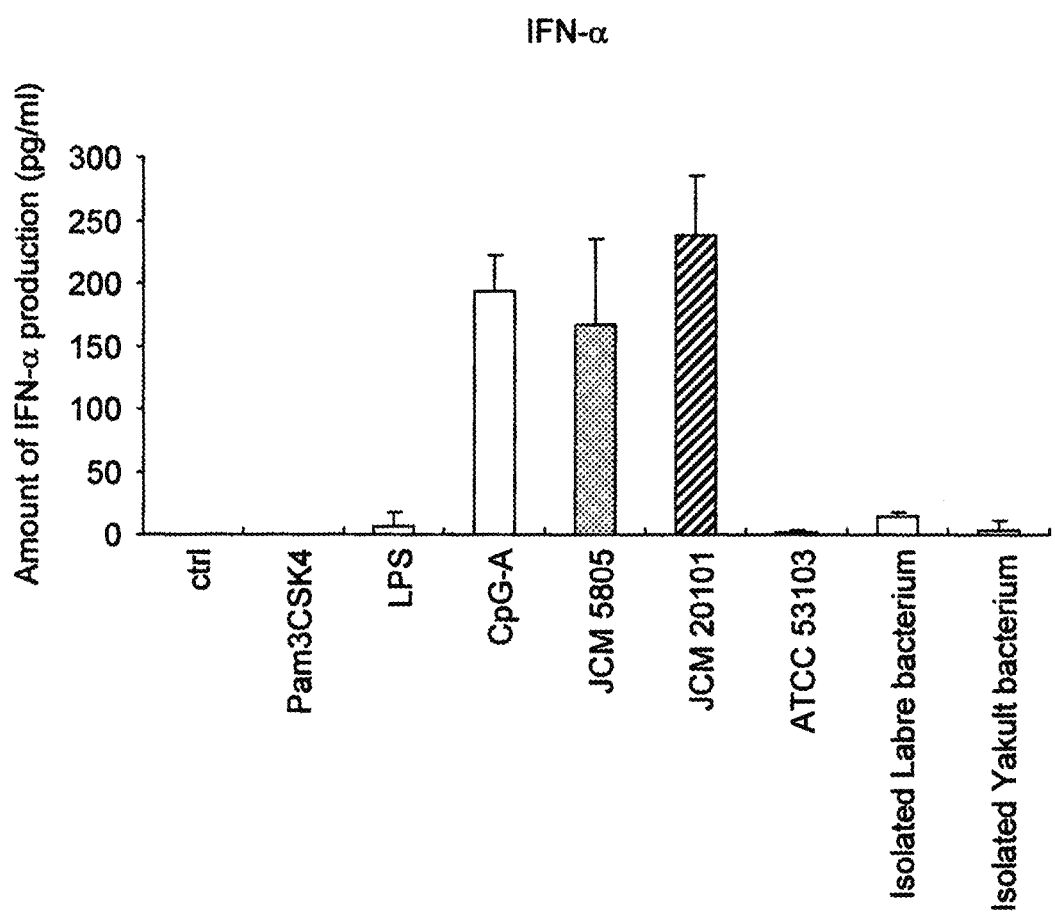
FIG. 5A shows the amount of IFN-α production from various lactic acid bacteria.
Figure 5B:
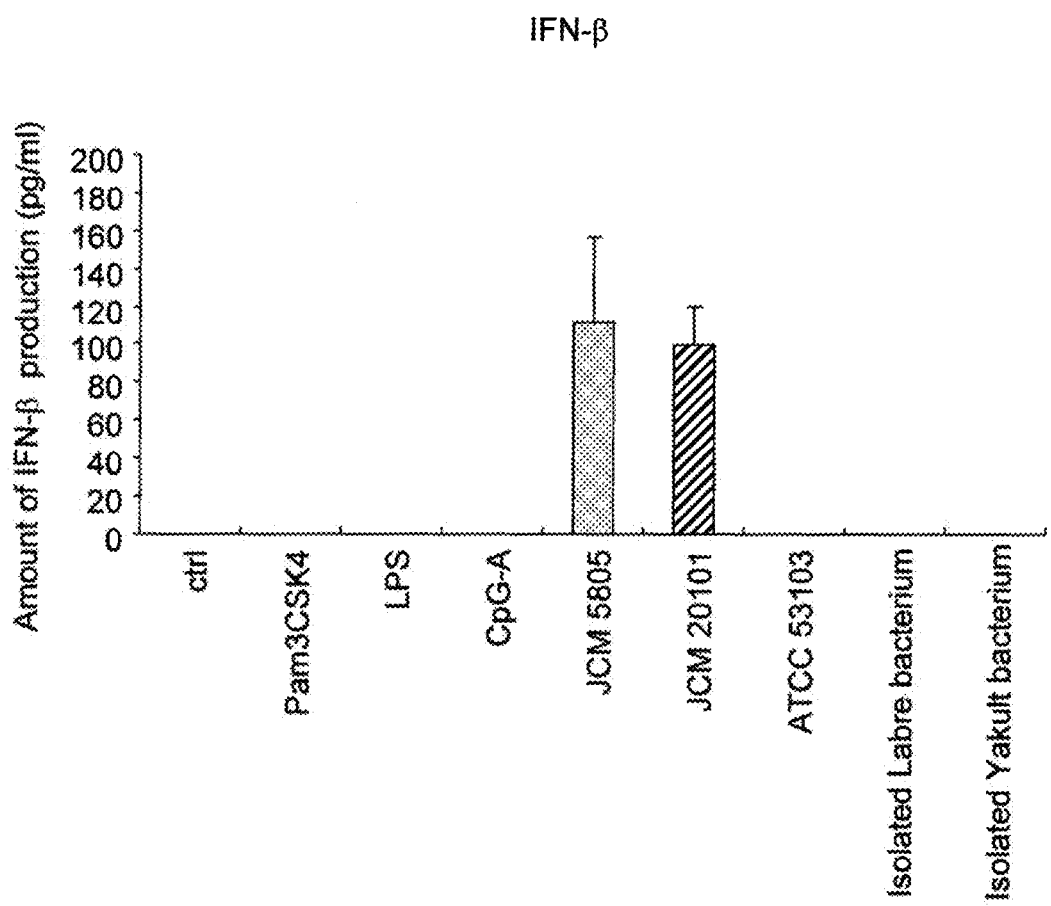
FIG. 5B shows the amount of IFN-β production from various lactic acid bacteria.
Figure 5C:
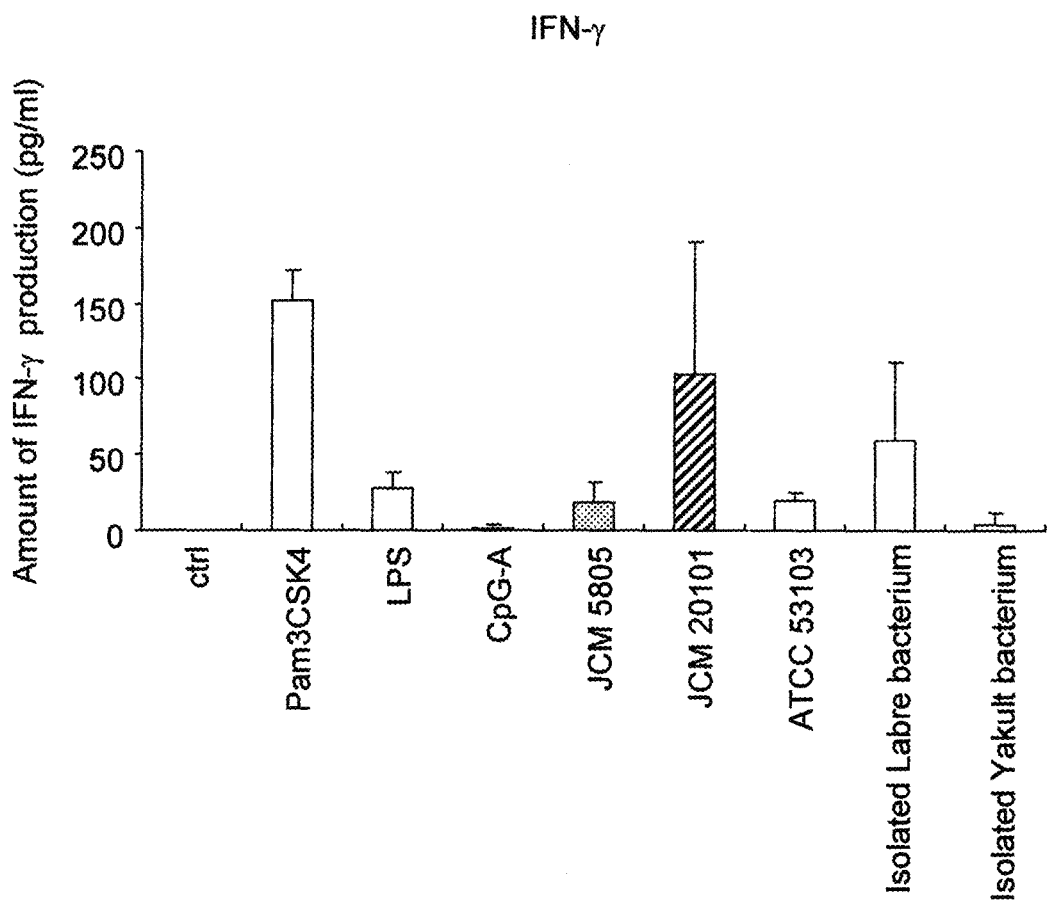
FIG. 5C shows the amount of IFN-γ production from various lactic acid bacteria.
Figure 5D:
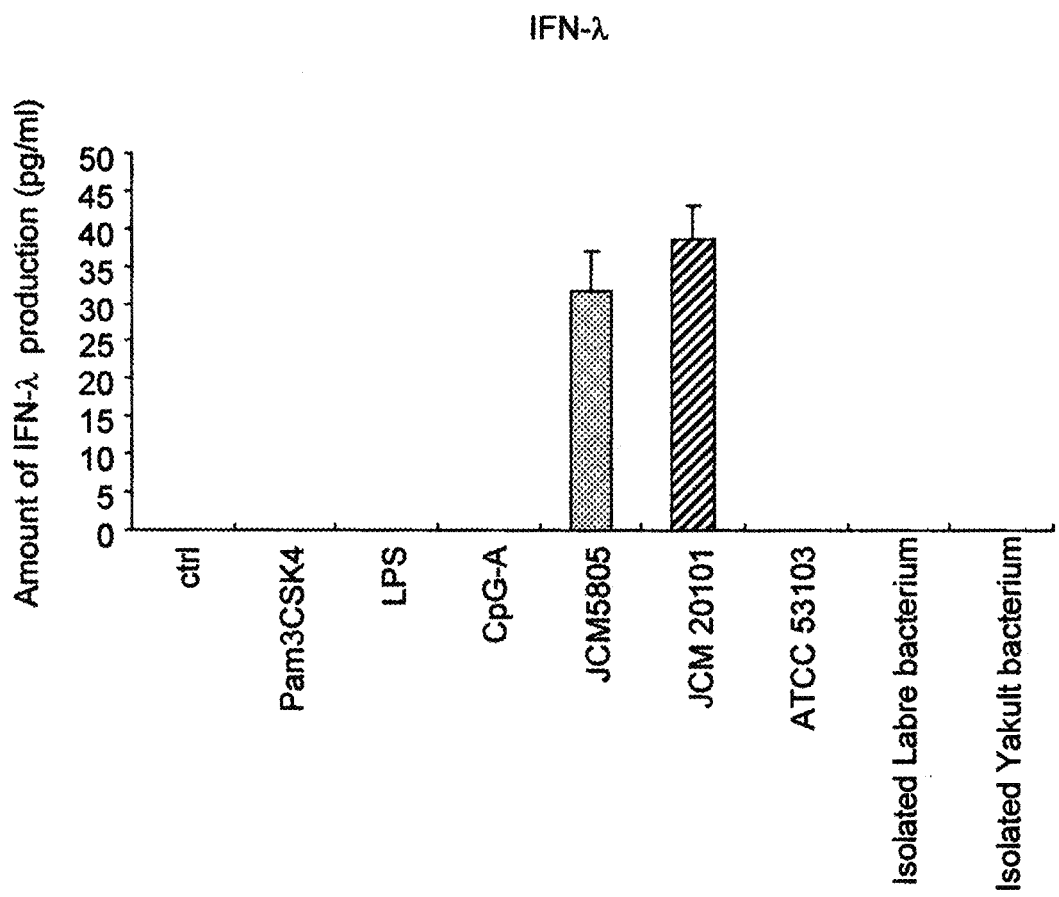
FIG. 5D shows the amount of IFN-λ, production from various lactic acid bacteria.

FIGS. 3A and 3B show electron micrographs of the *Lactococcus lactis* JCM5805 and JCM20101 strains. FIG. 3A shows the JCM5805 strain, and FIG. 3B shows the JCM20101 strain. These strains were oval-shaped bacteria with approximately 1-µm major axes and 0.5-µm minor axes. Since rod-shaped bacteria generally have approximately 1-µm minor axes and 3-µm major axes, it can be said that such bacteria are very small.

Example 3

Differences in Lactic Acid Bacteria Recognition (Uptake) by pDCs

With the use of the *Lactococcus lactis* JCM5805 and JCM20101 strains, which were found to be pDC-activating lactic acid bacteria in Example 2, and *Lactobacillus rhamnosus* ATCC53103 as a negative control, an experiment was carried out to confirm that activity would depend on recognition of the bacteria by pDCs; i.e., uptake of the bacteria.

<Experimental Method>

In Example 2, bone marrow cells were cultured by laying a micro glass cover slip (Matsunami Glass Ind., Ltd.). *Lactococcus lactis* JCM5805, *Lactococcus lactis* JCM20101, and *Lactobacillus rhamnosus* ATCC53103 labeled with FITC (SIGMA) were added thereto, and culture was conducted in a $CO_2$ incubator at 37° C. in the presence of 5% $CO_2$ for 3 hours. Thereafter, the micro glass cover slip was collected. The cells were stained with anti-B220-PE-Cy5.5 (eBiosciencs), allowed to adhere to the glass slides (Matsunami Glass Ind., Ltd.), and then observed under a fluorescent microscope (Olympus Corporation).

<Results>

The results are shown in FIGS. 4A-4D. FIG. 4A, FIG. 4B, and FIG. 4C show *Lactococcus lactis* JCM5805, the *Lactococcus lactis* JCM21101 strain, and *Lactobacillus rhamnosus* ATCC53103, respectively. B220-positive red cells are pDCs. In the *Lactococcus lactis* JCM5805 and JCM20101 strains, uptake of the lactic acid bacteria stained green into cells is observed, although *Lactobacillus rhamnosus* ATCC53103 is not incorporated into the cells. Therefore, whether or not activity occurs is considered to depend on the recognition of bacteria by pDCs.

Example 4

Activity of Lactic Acid Bacteria in Terms of Capacity for Inducing IFN Production The capacity of the lactic acid bacteria having the capacity for inducing IFN-α production for producing cytokines of other types was examined.

<Experimental Method>

The killed and lyophilized products (10 µg/ml) of *Lactococcus lactis* JCM5805, *Lactococcus lactis* JCM20101, and *Lactobacillus rhamnosus* ATCC53103 and, as positive controls, known TLRLs; i.e., Pam3CSK4 (TLR2L, 1 µg/ml, InvivoGen), LPS (TLR4L, 5 ng/ml, SIGMA-ALDRICH), and CpG DNA (TLR9L, 0.1 µM, InvivoGen), were added to the pDC/mDC culture system described in Example 2, and the culture supernatant was recovered 48 hours later. The culture supernatant was subjected to ELISA assays using the IFN-α assay kit (PBL), the IFN-β assay kit (PBL), the IFN-γ assay kit (BD Pharmingen), and the IL-28/IFN-λ, assay kit (eBiosciencs).

<Results>

The results are shown in FIG. 5A to FIG. 5D. FIG. 5A, FIG. 5B, FIG. 5C, and FIG. 5D show the results concerning IFN-α, IFN-β, IFN-γ, and IFN-λ, respectively. As described in Example 2, the capacity for IFN-α production was observed in *Lactococcus lactis* JCM5805 and in *Lactococcus lactis* JCM20101, and the titer thereof was equivalent to that of CpG DNA (ODN 1585) (i.e., TLR9L, 0.1 µM). Concerning IFN-β, which is also type I IFN, the capacity was observed selectively in the *Lactococcus lactis* JCM5805 and JCM20101 strains. Concerning IFN-γ, which is type II IFN, all bacterial strains exerted the capacity for inducting production, although the degree thereof varied among bacterial species. Concerning IFN-γ, which is type III IFN, induction was observed selectively in *Lactococcus lactis* JCM5805 and in *Lactococcus lactis* JCM20101.

While the level of IFN-λ, induced by IFN-stimulated genes (ISG) is known to be lower than that of IFN-α or IFN-β, IFN-λ, is known to potentiate its antiviral effects in coordination with IFN-α (Non-Patent Document 5). Since the *Lactococcus lactis* JCM5805 and JCM20101 strains are capable of inducing production of all of type I, type II, and type III IFNs, these strains are considered to have very strong antiviral activity.

Example 5

Activity of Lactic Acid Bacteria in Terms of pDC Activation

The capacity of lactic acid bacteria having the capacity for inducing IFN-α production for pDC activation was examined.

<Experimental Method>

The cells cultured in Example 3 were stained for 30 minutes at 4° C. with the use of anti-CD11b-APC-Cy7 antibody (BD Pharmingen), anti-B220-PerCP antibody (BD Pharmingen), and anti-CD11c-PE-Cy7 antibody (eBiosciencs) for pDC gating, anti-MHC class II-FITC antibody (eBiosciencs), anti-CD40-FITC antibody (eBiosciencs), anti-CD80-APC antibody (eBiosciencs), and anti-CD86-APC antibody (eBiosciencs) as indicators for activation, and anti-OX40L-PE antibody (eBiosciencs), anti-PDL-1-PE antibody (eBiosciencs), and anti-ICOS-L-PE antibody (eBiosciencs) as inhibitory markers. The cells were washed and then analyzed with the use of FACS Canto II (BD).

<Results>

Figure 6A:
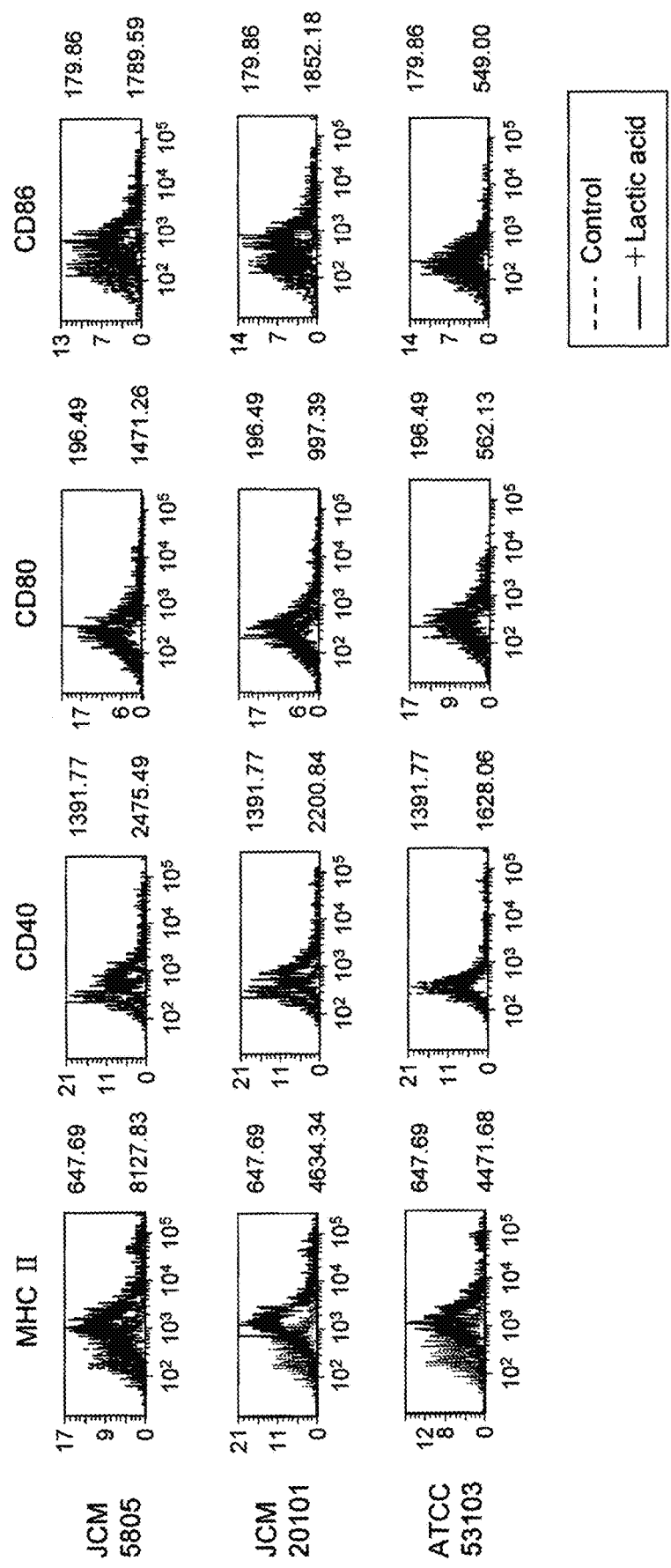
FIG. 6A shows the capacity for pDC activation of lactic acid bacteria having the capacity for inducing IFN-α production and the expression levels of MHCII, CD40, CD80, and CD86.
Figure 6B:
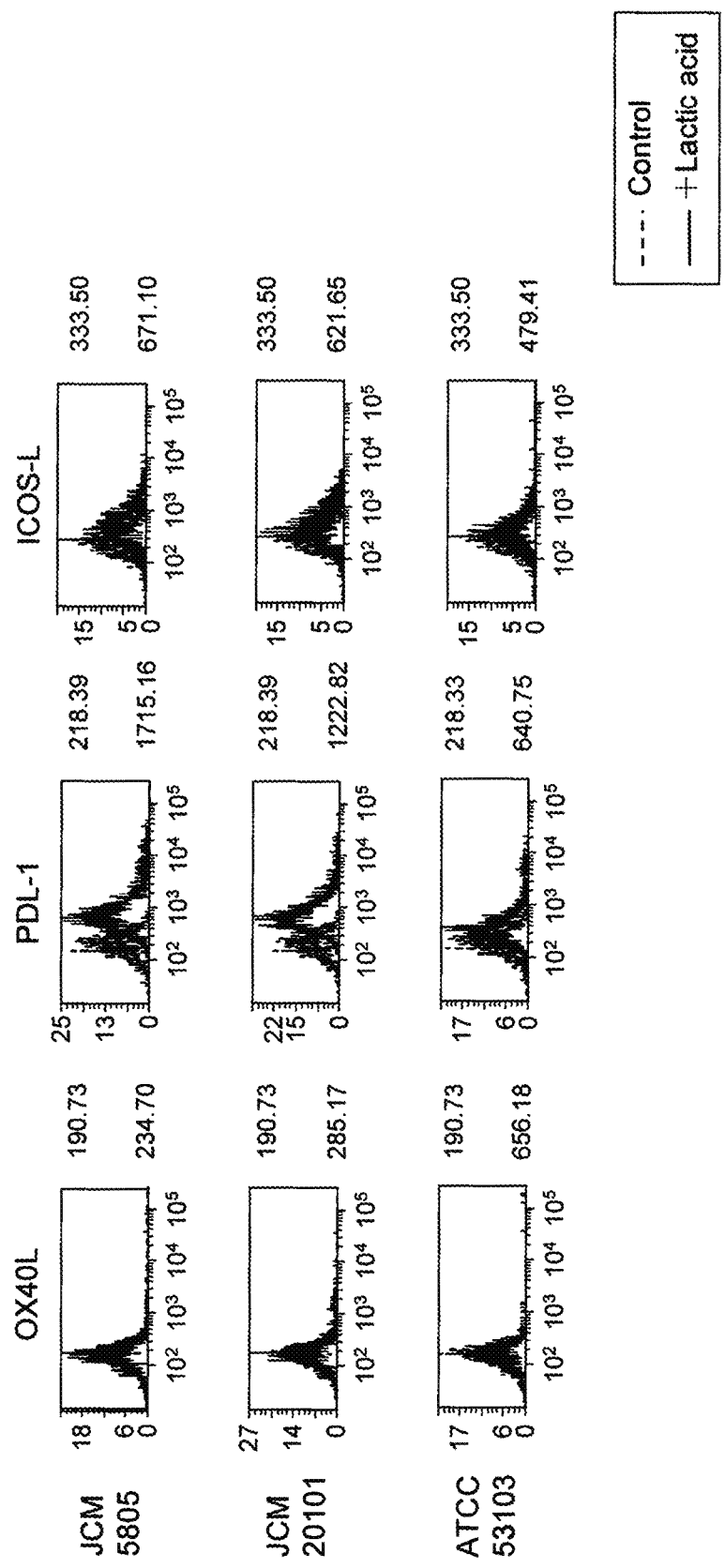
FIG. 6B shows the capacity for pDC activation of lactic acid bacteria having the capacity for inducing IFN-α production and the expression levels of OX40L, PDL-1, and ICOS-L.

The results are shown in FIG. 6A and in FIG. 6B. FIG. 6A shows MHCII, CD40, CD80, and CD86 expression levels, and FIG. 6B shows OX40L, PDL-1, and ICOS-L expression levels. The median fluorescent intensity values (MFI) attained without the addition of lactic acid bacteria are shown above, and the MFI values attained with the addition of lactic acid bacteria are shown below. According to the activation markers, enhancement was observed with the addition of any lactic acid bacteria. The greatest difference between the *Lactococcus lactis* JCM5805 and JCM20101 strains and the *Lactobacillus rhamnosus* ATCC53103 strain having no capacity for inducing IFN-α production is observed in CD28, which is a T cell activity regulatory molecule, and CTLA-4 ligands (i.e., CD80 and CD86). Expression levels were significantly enhanced by the *Lactococcus lactis* JCM5805 and JCM20101 strains. According to the inhibitory markers, an increase was observed in the expression levels with the addition of lactic acid bacteria, as expected. In particular, PDL-1 expression was significantly activated by the *Lactococcus lactis* JCM5805 and JCM20101 strains.

As described above, pDCs stimulated by the *Lactococcus lactis* JCM5805 and JCM20101 strains produce IFN-α, thereby potentiating the immune system. However, the potentiated immune system may cause autoimmune diseases as side effects. PDL-1, which was confirmed to be induced upon stimulation by the *Lactococcus lactis* JCM5805 and JCM20101 strains in this test, is known to bind to PD-1 of the T cell to induce a regulatory T cell. Specifically, the *Lactococcus lactis* JCM5805 and JCM20101 strains are considered to be capable of maintenance of the immune system in a well-balanced state while refraining from being excessively activated through PDL-1 expression, in addition to potentiation of the immune system through IFN-α production.

Example 6

Capacity for Stimulating IFN-α Production of Lactic Acid Bacteria in the Presence of Either or Both pDCs and mDCs In Example 2, the *Lactococcus lactis* JCM5805 and JCM20101 strains were selected on the basis of activity for inducing IFN-α production. In the culture system used for assays, myeloid dendritic cells (mDCs) develop, in addition to pDCs (i.e., a so-called pDC/mDC mixed culture system). The pDC-mDC interactions are considered to be critical in an organism. For example, conversion of pDC into mDC upon virus infection has been reported. Accordingly, the effects of the addition of lactic acid bacteria in the pDC or mDC monoculture system, the pDC/mDC mixed culture system, and the mixed culture system in which pDCs were physically separated from mDCs were examined.

<Experimental Method> pDCs and mDCs induced from bone marrow cells with the aid of Flt-3L were subjected to mixed culture in the same manner as in Example 2, and pDCs were separated from mDCs using FACS Aria (BD). Subsequently, pDCs and mDCs were subjected to culture at a density of $1 \times 10^5$ cells/ml under the conditions described below: (1) in a monoculture system in which pDCs are separated from mDCs (indicated as pDC or mDC); (2) in a mixed culture system in which pDCs are physically in contact with mDCs (pDC:mDC=1:1); and (3) a pDC/mDC co-culture system in which physical contact between pDCs and mDCs is blocked with a semipermeable membrane (indicated as pDC/mDC or mDC/pDC, cells cultured on a semipermeable membrane and in contact with lactic acid bacteria are shown on the left). Transwell filter (Corning) was used as a semipermeable membrane, and the amount of lactic acid bacteria added was 10 μg/ml. Culture was conducted for 2 days and the amount of IFN-α in the culture supernatant was then assayed. As a positive control, CpG DNA (ODN1585), the capacity of which for pDC activation has been known, was used at 0.1 μM. Sorted pDCs were attached to glass slides (Matsunami glass Ind., Ltd) using Cytospin (Thermo Scientific), stained with Diff-Quick (Sysmex), and then observed under a microscope (Olympus Corporation).

<Results>

Figure 7:
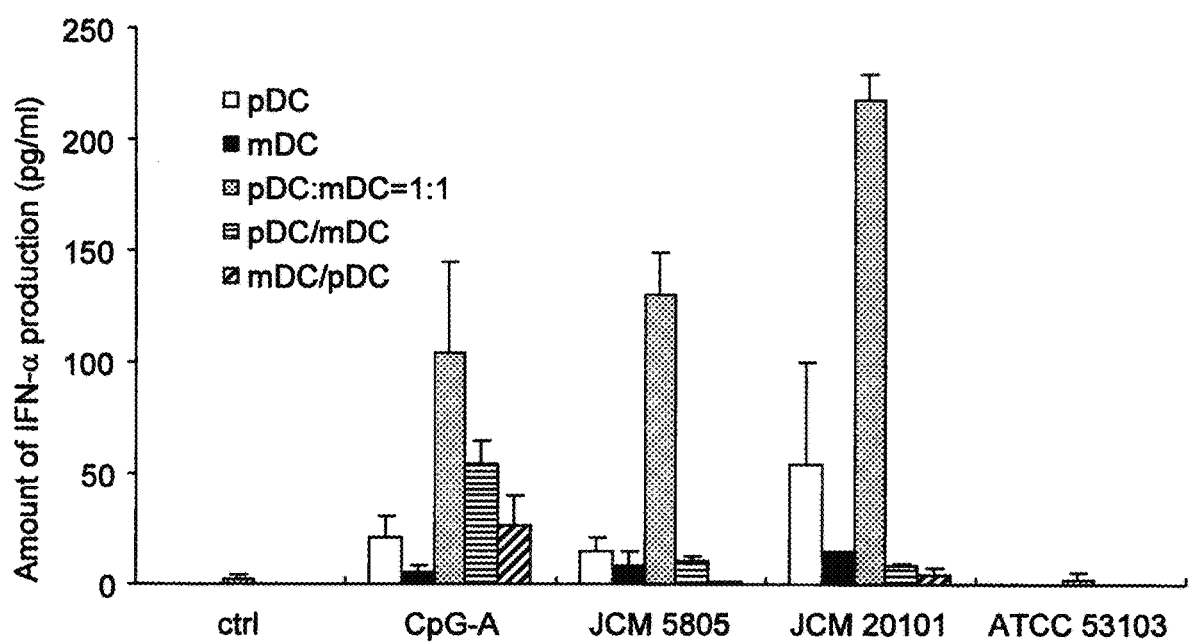
FIG. 7 shows the capacity for stimulating IFN-α production of lactic acid bacteria in the presence of either or both pDCs and mDCs.

The results are shown in FIG. 7. The *Lactococcus lactis* JCM5805 and JCM20101 strains exhibited similar responses. Specifically, IFN-α production did not take place in the mDC monoculture system, a small quantity of IFN-α was induced in the pDC monoculture system, and a significant level of IFN-α production was observed in the pDC/mDC mixed culture system. FIGS. 8A-8D show configurations of pDCs when *Lactococcus lactis* JCM5805, *Lactococcus lactis* JCM20101, and *Lactobacillus rhamnosus* ATCC53103 are added to the pDC monoculture system. FIG. 8A shows the results of a control (without the addition of lactic acid bacteria), FIG. 8B shows pDCs when JCM5805 was added, FIG. 8C shows pDCs when JCM20101 was added, and FIG. 8D shows pDCs when ATCC53103 was added. As a result of a comparison of pDCs upon the addition of the *Lactococcus lactis* JCM5805 and JCM20101 strains and pDCs without the addition thereof, a cell process characteristic of an activated dendritic cell was apparently observed when the *Lactococcus lactis* JCM5805 and JCM20101 strains were added. When *Lactobacillus rhamnosus* ATCC53103 was added, however, a process as observed when the *Lactococcus lactis* JCM5805 or JCM20101 strain was added was not detected. More interestingly, the level of IFN-α production was drastically reduced to a level equivalent to that attained in the pDC monoculture when physical contact between pDCs and mDCs was blocked with a semipermeable membrane. Thus, it was found that the presence of mDCs would be necessary in order to fully induce IFN-α production via activation of pDC, although pDCs are primary targets of lactic acid bacteria. In addition, the mDC/pDC cross-talk was found to be mediated by a cell-to-cell contact instead of a humoral factor. Since substantially the same phenomenon is observed with the addition of CpG DNA, it was verified that a role of mDC in such pDC activation would be a universal mechanism that would not be limited to a particular substance (i.e., lactic acid bacteria). Both pDCs and mDCs are present in a human body, and such mechanism would serve as a key factor when considering application thereof to humans.

Example 7

Identification of Receptors Involved

Signals essential for the *Lactococcus lactis* JCM5805 and JCM20101 strains to produce IFN-α were examined using TLR knockout mice.

<Experimental Method>

TLR2-, TLR4-, TLR7-, TLR9-, and MyD88-knockout mice (8- to 10-week-old, male) and wild-type C57BL/6 mice (8- to 10-week-old, male) were purchased from Charles River Laboratories. pDCs and mDCs were induced from bone marrow cells of such mice in the same manner as in Example 2, and *Lactococcus lactis* JCM5805, *Lactococcus lactis* JCM20101, and *Lactobacillus rhamnosus* ATCC53103 were added. In addition to the 3 TLRLs described in Example 3, TLR7L (ssRNA40, 5 µg/ml, InvivoGen) was used as a positive control. The culture supernatant was collected 48 hours later, and the amount of IFN-α produced in the culture supernatant was assayed via ELISA.

<Results>

Figure 9B:
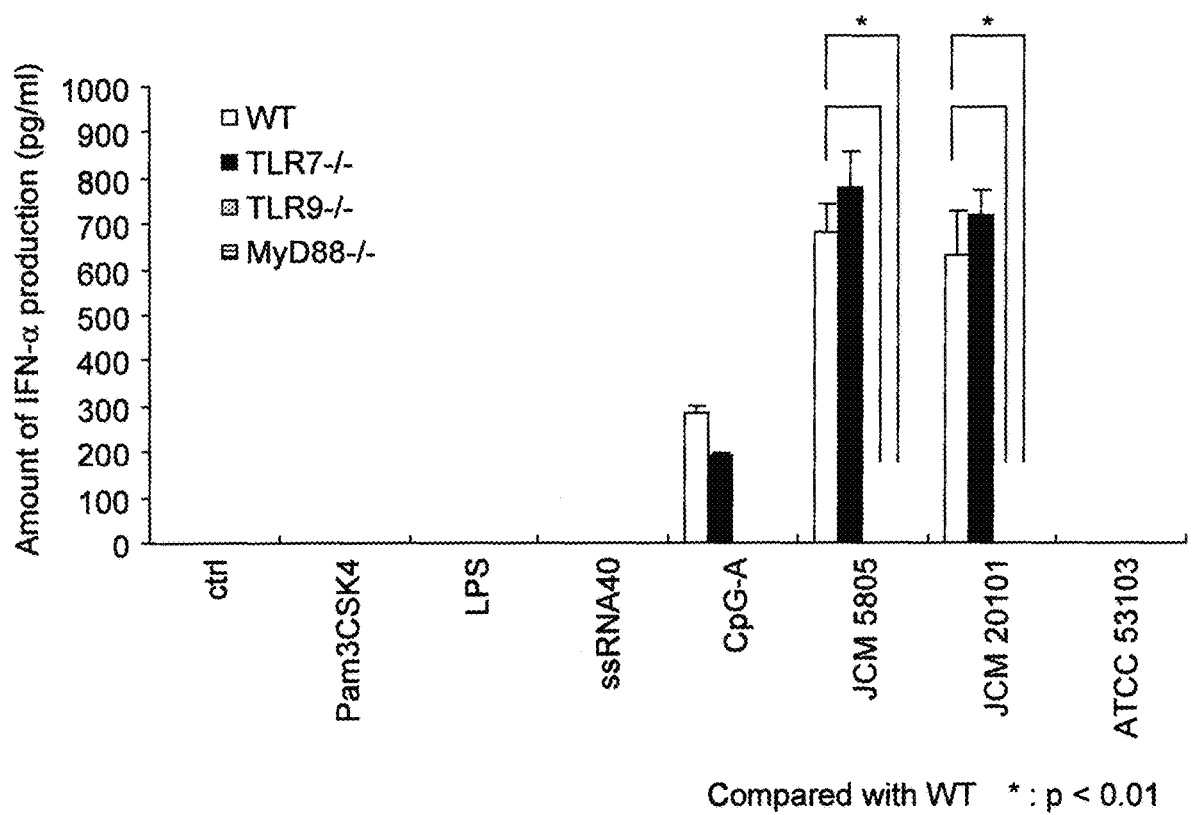
FIG. 9B shows the amounts of IFN-α production when *Lactococcus lactis* JCM5805, *Lactococcus lactis* JCM20101, and *Lactobacillus rhamnosus* ATCC53103 are added to the pDC/mDC cells generated from TLR7, TLR9, and MyD88 knockout mice.

The results are shown in FIG. 9A and in FIG. 9B. FIG. 9A shows the results concerning TLR2-knockout mice and TLR4-knockout mice, and FIG. 9B shows the results concerning TLR7-knockout mice, TLR9-knockout mice, and MyD88-knockout mice. In the figures, "WT" represents the results concerning wild-type mice. No changes in the capacity for IFN-α production of the *Lactococcus lactis* JCM5805 and JCM20101 strains were observed in TLR2- or TLR4-knockout mice, and the involvement thereof was accordingly denied. When either of the *Lactococcus lactis* JCM5805 or JCM20101 strain was added to mice, IFN-α in TLR9- and MyD88-knockout mice completely disappeared by the knocking out of TLR9 and MyD88, respectively. Accordingly, TLR9 was verified to play a key role in IFN-α production by the *Lactococcus lactis* JCM5805 and JCM20101 strains.

Example 8

Identification of Active Substance

In Example 5, TLR9 was found to be a recognition receptor for the *Lactococcus lactis* JCM5805 and JCM20101 strains. Identification of the ligands thereof was attempted. DNA represented by CpG DNA is known as a TLR9 ligand. Concerning RNA, which is also a nucleic acid, ssRNA represented by the RNA virus is known as TLR7L, and dsRNA is known as TLR3L. Since DNA or RNA was deduced to be a ligand, DNA and RNA were extracted from both strains in order to inspect the activity.

<Experimental Method>

Preparation of DNA from Lactic Acid Bacteria

In accordance with the procedure of Example 1, *Lactococcus lactis* JCM5805, *Lactococcus lactis* JCM20101, and *Lactobacillus rhamnosus* ATCC53103 were subjected to stationary culture. The strains were harvested and then washed three times with sterile water. A solution adjusted to comprise 50 mM Tris-HCl, 5 mM EDTA, and 6.7% sucrose (PH 8.0) was added thereto. Subsequently, N-acetylmuramidase (2.5 mg/ml, Seikagaku Kogyo) and lysozyme (50 mg/ml, Seikagaku Kogyo) were added, and the resultant was allowed to stand at 37° C. for 45 minutes. Further, 50 mM Tris-HCl, 250 mM EDTA (PH 8.0), and 10% SDS were added thereto, and the resultant was allowed to stand at 37° C. for 10 minutes. 5.0 M NaCl was added, phenol, chloroform, and isoamyl alcohol (Wako Pure Chemicals Industries, Ltd.,) were added thereto, and the mixture was subjected to centrifugation. The supernatant was selectively recovered, ethanol in an amount twice the amount of the supernatant was added thereto, and the resultant was then subjected to centrifugation. The supernatant was removed, 70% ethanol was added to the precipitate, and centrifugation was then carried out. The supernatant was removed, RNase (Qiagen) was added thereto, and the resultant was allowed to stand at 37° C. for 60 minutes. Further, 5.0 M NaCl was added thereto, phenol, chloroform, and isoamyl alcohol (Wako Pure Chemicals Industries, Ltd.,) were added thereto, and the mixture was subjected to centrifugation. The supernatant was selectively removed, ethanol in an amount twice the amount of the supernatant was added thereto, and the resultant was then subjected to centrifugation. The supernatant was removed, 70% ethanol was added to the precipitate, and centrifugation was then carried out. Nuclease Free Water (Qiagen) was added to the precipitate from which the supernatant had been removed. DNAs of *Lactococcus lactis* JCM5805, *Lactococcus lactis* JCM20101, and *Lactobacillus rhamnosus* ATCC53103 prepared in the manner described above were added to the pDC/mDC culture system at 0.1 µg/ml, 1 µg/ml, and 10 µg/ml, respectively. The supernatant was collected 48 hours later, and the amount of IFN-α produced in the culture supernatant was assayed via ELISA. The bacterial strains were used as controls.

Preparation of Total RNA from Lactic Acid Bacteria

In accordance with the procedure of Example 1, *Lactococcus lactis* JCM5805, *Lactococcus lactis* JCM20101, and *Lactobacillus rhamnosus* ATCC53103 were subjected to stationary culture. The strains were harvested and then washed three times with sterile water. RNA protect Bacteria Reagent (Qiagen) was added thereto, and the resultant was allowed to stand at 37° C. for 5 minutes, followed by centrifugation. The supernatant was removed, lysozyme (5 mg/ml, Seikagaku Kogyo) was added, and the resultant was allowed to stand at 37° C. for 10 minutes. Thereafter, total RNAs were prepared from *Lactococcus lactis* JCM5805, *Lactococcus lactis* JCM20101, and *Lactobacillus rhamnosus* ATCC53103 through DNase treatment (Qiagen) with the use of RNeasy Mini Kit (Qiagen). Total RNAs were added to the culture system according to Example 3 at 0.1 µg/ml, 1 µg/ml, and 10 µg/ml, respectively. The culture supernatant was collected 48 hours later, and the amount of IFN-α produced in the culture supernatant was assayed via ELISA. The bacterial strains were used as controls.

<Results>

Figure 10:
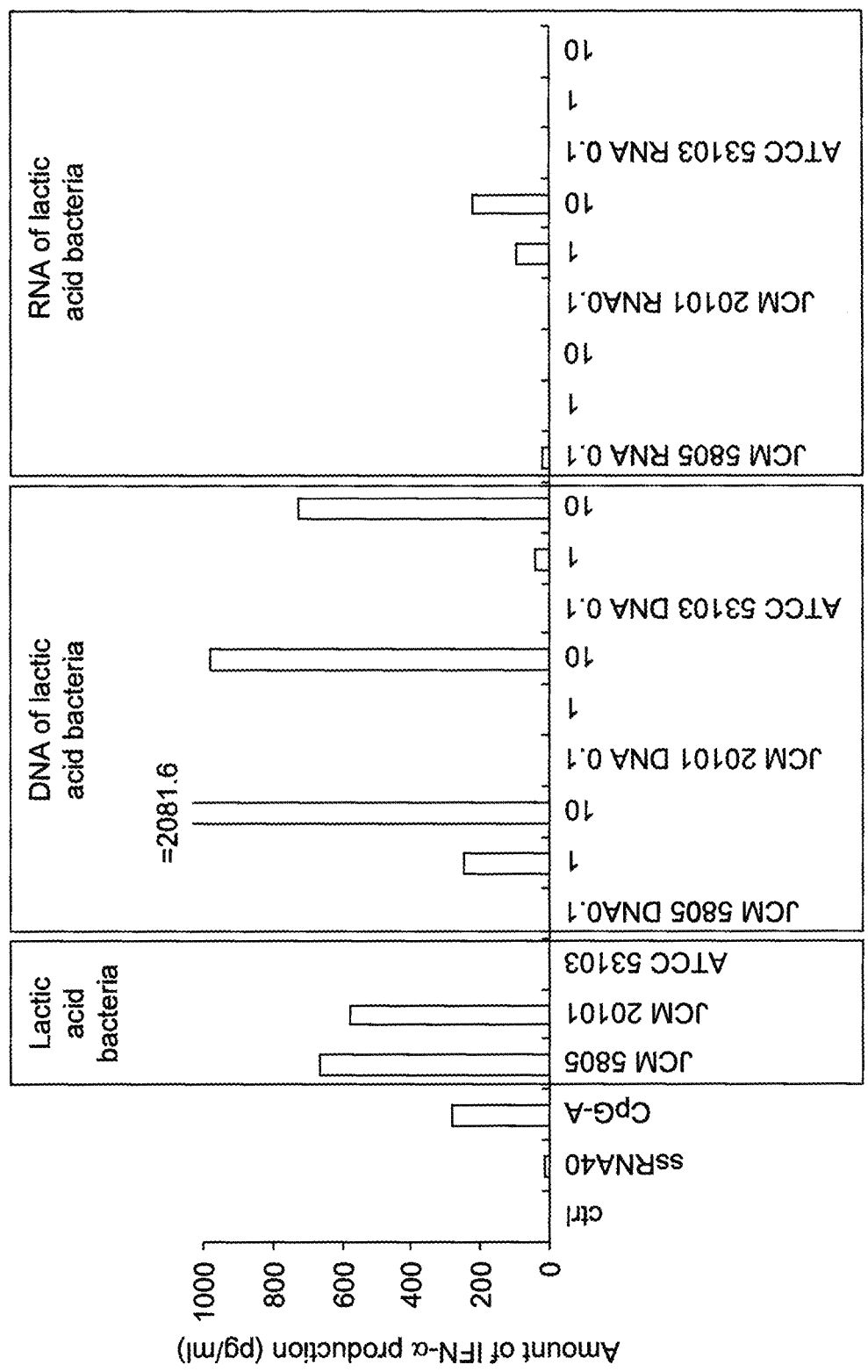
FIG. 10 shows the capacity for IFN-α activation of DNAs and RNAs of *Lactococcus lactis* JCM5805 and *Lactococcus lactis* JCM20101.

The results are shown in FIG. 10. DNAs of the *Lactococcus lactis* JCM5805 and JCM20101 strains were found to have strong activity for inducing IFN-α, as expected. Activity was apparently detected when *Lactococcus lactis* JCM5805 was added at 1 µg/ml and when *Lactococcus lactis* JCM20101 was added at 10 µg/ml. While no activity was detected in *Lactobacillus rhamnosus* ATCC53103, DNA thereof was found to exert activity at a level equivalent to that of *Lactococcus lactis* JCM20101. More surprisingly, activity was detected when total RNA of *Lactococcus lactis* JCM20101 was added, and IFN-α production was induced at 1 µg/ml or higher.

These results demonstrate the following: (1) DNA is the active substance of activity for inducing IFN-α production and DNA of an inactive strain has activity; and (2) since lactic acid bacteria that activate pDCs and induce IFN-α represented by the *Lactococcus lactis* JCM5805 and JCM20101 strains are recognized by pDCs as strains, activity is detected without performing DNA extraction. A strain such as *Lactobacillus rhamnosus* ATCC53103 is inactive because it is not recognized by pDC; and (3) RNA of lactic acid bacteria becomes active besides DNA and it functions as TLRL, although it is very rare. If the examples mentioned above are taken into consideration, RNA of *Lactococcus lactis* JCM20101 is the RNA ligand for TLR9, the ligand of which has been known to be DNA, discovered for the first time.

Example 9

Examination of Effects of Ingestion of *Lactococcus lactis* JCM5805 Using Healthy Mice In the examples above, some lactic acid bacteria were found to have the capacity for pDC activation and for induction of IFN-α production in vitro. Thus, *Lactococcus lactis* JCM5805 was designated as a representative example and examined regarding the immunostimulatory effects in vivo attained via oral administration.
<Experimental Method>

Figure 11:
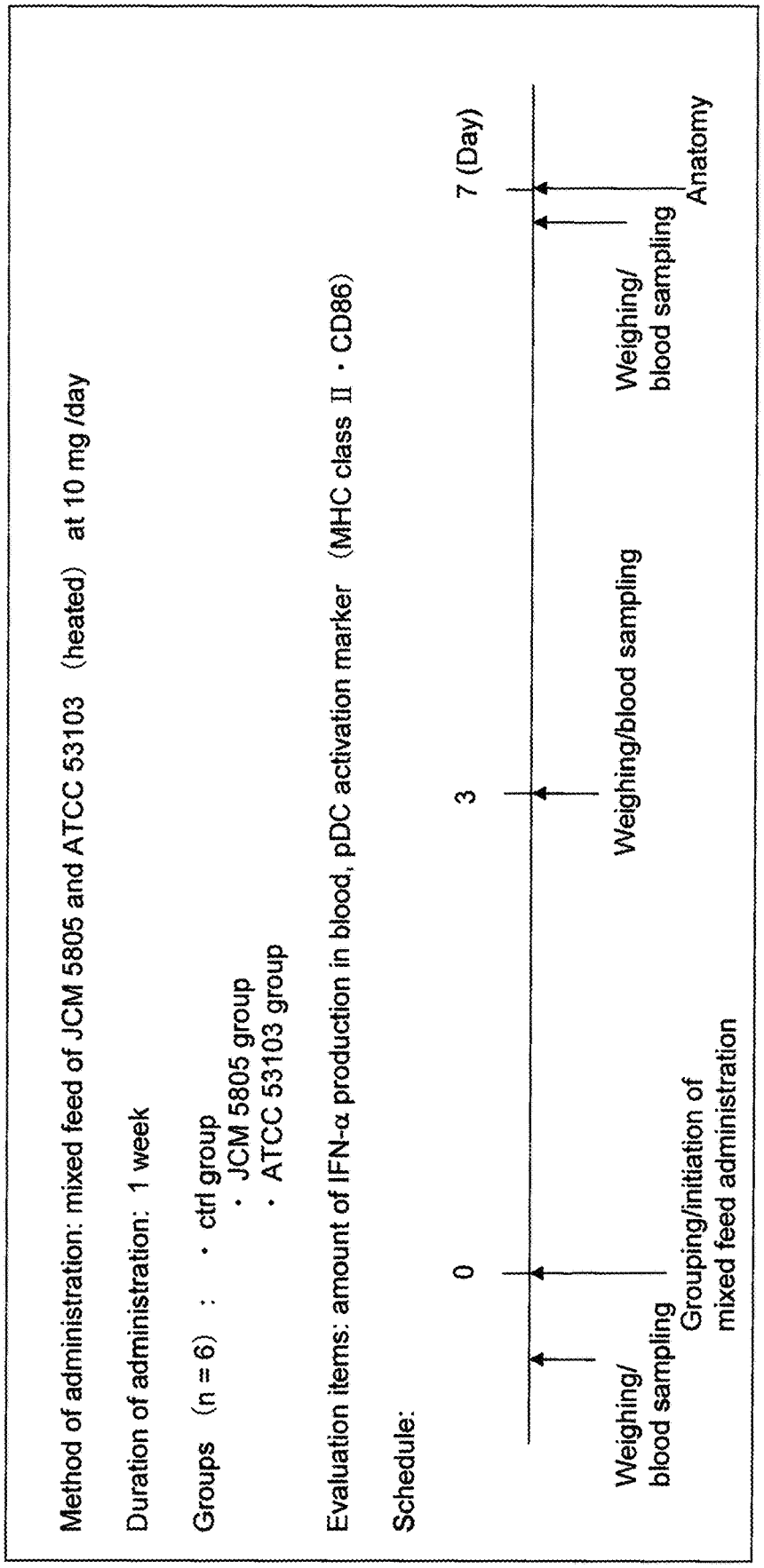
FIG. 11 shows a summary of the experimental design examining the effects of ingestion of *Lactococcus lactis* JCM5805 using healthy mice.

Three groups of C57BL/6 mice (7-week-old, female) each consisting of 5 individuals were provided: a group to which standard feeds (AIN93G, Oriental Yeast Co., Ltd.) are administered; a group to which mixed feeds containing *Lactococcus lactis* JCM5805 are administered; and a group to which mixed feeds containing *Lactobacillus rhamnosus* ATCC53103 are administered. The dose of lactic acid bacteria was adjusted to 10 mg per mouse per day. Blood sampling was carried out on day 0, day 3, and day 7 (at the time of anatomy), and the amount of IFN-α produced in the blood was assayed via ELISA. At the time of anatomy, the spleen and the mesenteric lymph node were extracted, and low-density cell fractions containing enriched dendritic cells were prepared in the manner described below. (In accordance with a conventional technique, splenic lymphocytes and mesenteric lymph node lymphocytes are prepared, these cells are suspended in HBSS (Gibco) containing 20 mM HEPES (Gibco), and the resulting cell suspension is superposed on 10%-FCS-containing RPMI medium (Sigma) comprising Histodenz (Sigma-Aldrich) dissolved to a final concentration of 15%. After centrifugation, cells in the intermediate layer (i.e., low-density cell fractions) are recovered.) The low-density cell fractions were stained with anti-CD11b-APC-Cy7 antibody (BD Pharmingen), anti-mPDCA-1-APC antibody (Milteny Biotec), and anti-CD11c-PE-Cy7 antibody (eBiosciencs) for pDC gating and with anti-MHC class II-FITC antibody (eBiosciencs) and anti-CD86-PE antibody (eBiosciencs) as indicators for activation. The pDC gate (CD11c$^{int}$CD11b$^-$mPDCA-1$^+$) in vivo was determined via flow cytometry, and MHC class II and CD86 expression levels as pDC activation markers were assayed. FIG. 11 shows a summary of a method for examining the effects of *Lactococcus lactis* JCM5805 ingestion using healthy mice.
<Results>

Figure 12:
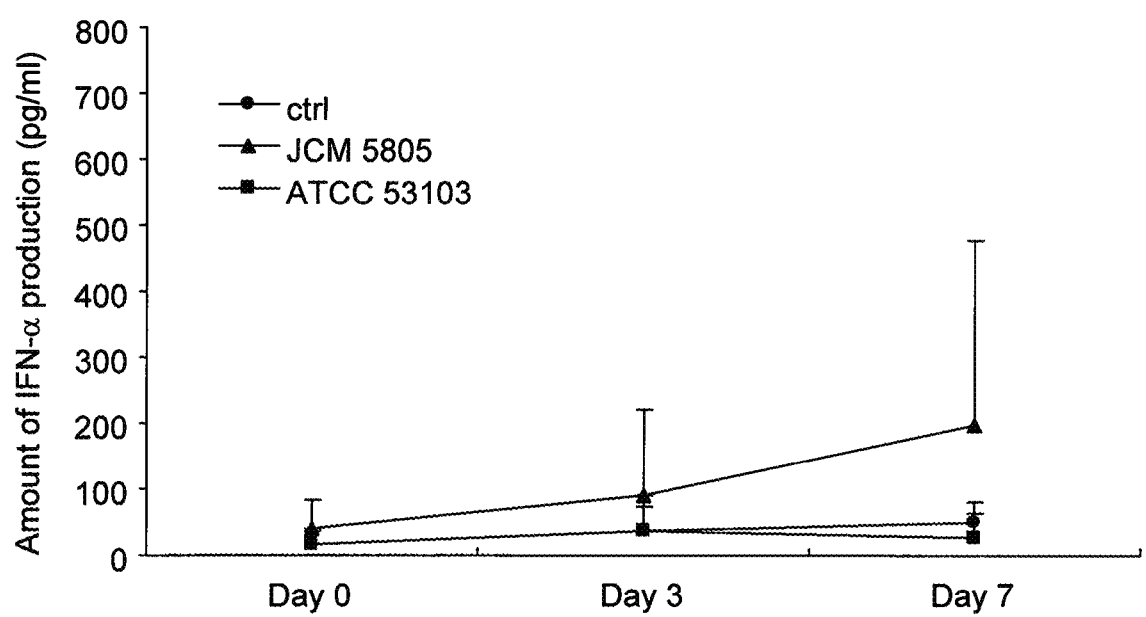
FIG. 12 shows changes in blood IFN-α levels of healthy mice that had ingested *Lactococcus lactis* JCM5805.
Figure 13A:
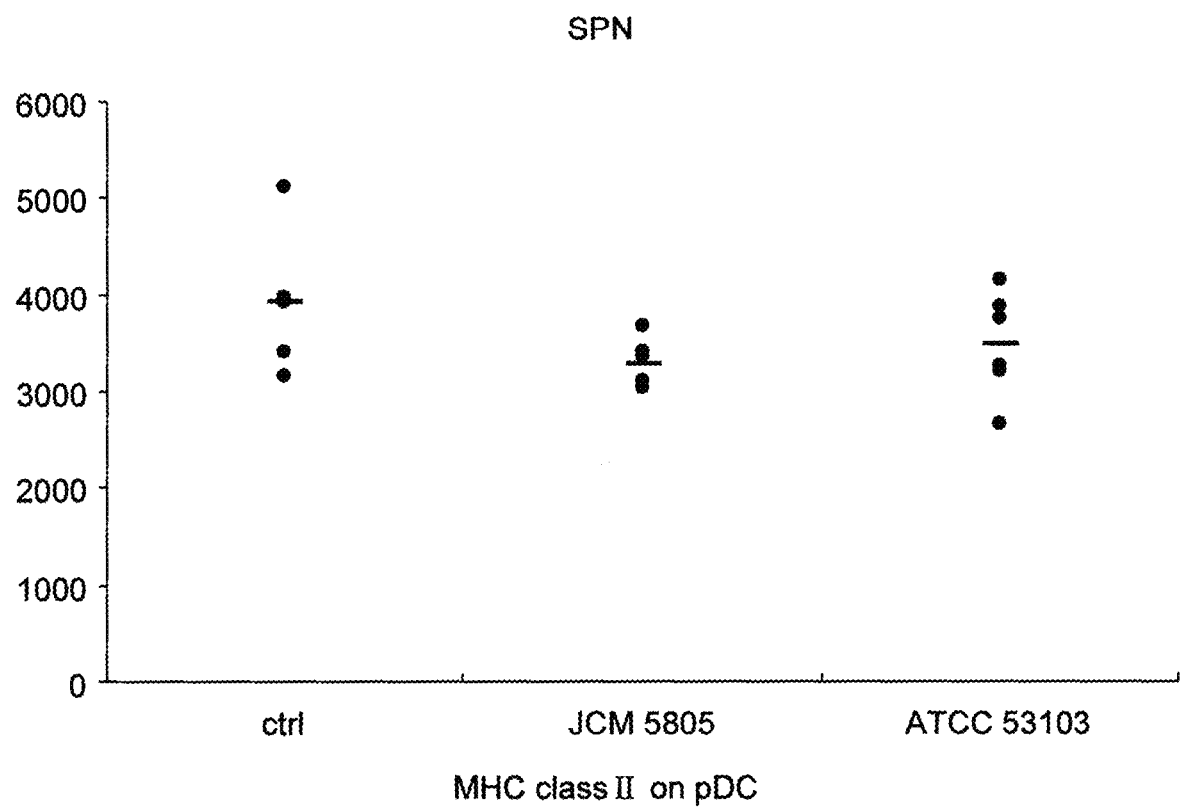
FIG. 13A shows changes in MEW class II levels in pDCs of the spleen of healthy mice that had ingested *Lactococcus lactis* JCM5805.
Figure 13B:
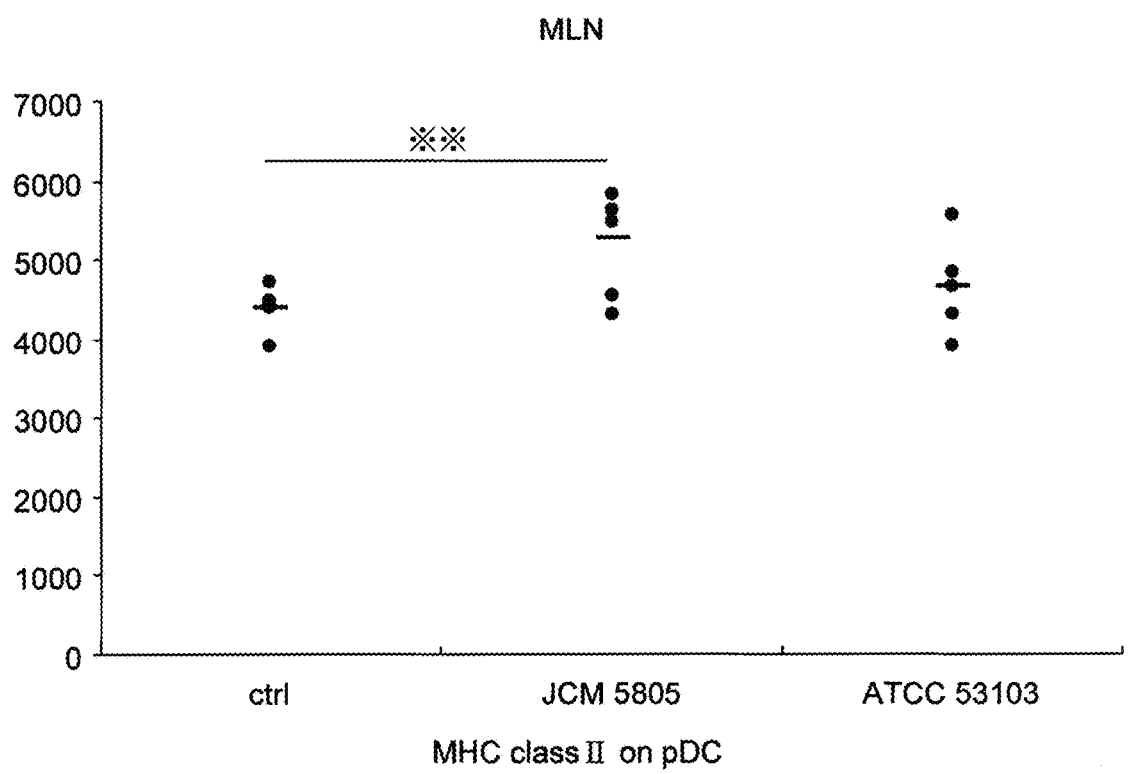
FIG. 13B shows changes in MEW class II levels in pDCs of the mesenteric lymph nodes of healthy mice that had ingested *Lactococcus lactis* JCM5805.

FIG. 12 shows the results of blood IFN-α assays, and FIG. 13A to FIG. 13D show the results of pDC activation. FIG. 13A and FIG. 13B show changes in MHC class II levels in pDCs of the spleen and the mesenteric lymph node, respectively, and FIG. 13C and FIG. 13D show changes in CD86 levels in pDCs of the spleen and the mesenteric lymph node, respectively. The blood IFN-α level did not increase at all in the group to which *Lactobacillus rhamnosus* ATCC53103 had been administered as in the case of the group to which the standard feeds had been administered. In contrast, upward trends in the IFN-α levels were observed on day 3 and day 7 in the group to which *Lactococcus lactis* JCM5805 had been administered (FIG. 12). Concerning pDC activation, changes in MHC class II or CD86 levels were not observed in either of the splenic or mesenteric lymph node lymphocytes of the group to which *Lactobacillus rhamnosus* ATCC53103 had been administered. While pDC activation did not take place in the spleen of the group to which *Lactococcus lactis* JCM5805 had been administered, a significant level of activation was observed in both MHC class II and CD86 in the mesenteric lymph node.

The above results indicate that *Lactococcus lactis* JCM5805 would stimulate pDCs in vivo, as well as in vitro, and it would be capable of inducing IFN-α production.

Example 10

Examination of Effects of JCM5805 Ingestion Using Immunosuppression Models

The lactic acid bacteria according to the present invention would be administered to persons with the weakened immune system or elderly people, as well as healthy persons. Thus, the effects of *Lactococcus lactis* JCM5805 ingestion were examined using immunosuppression models.
<Experimental Method>

Figure 14:
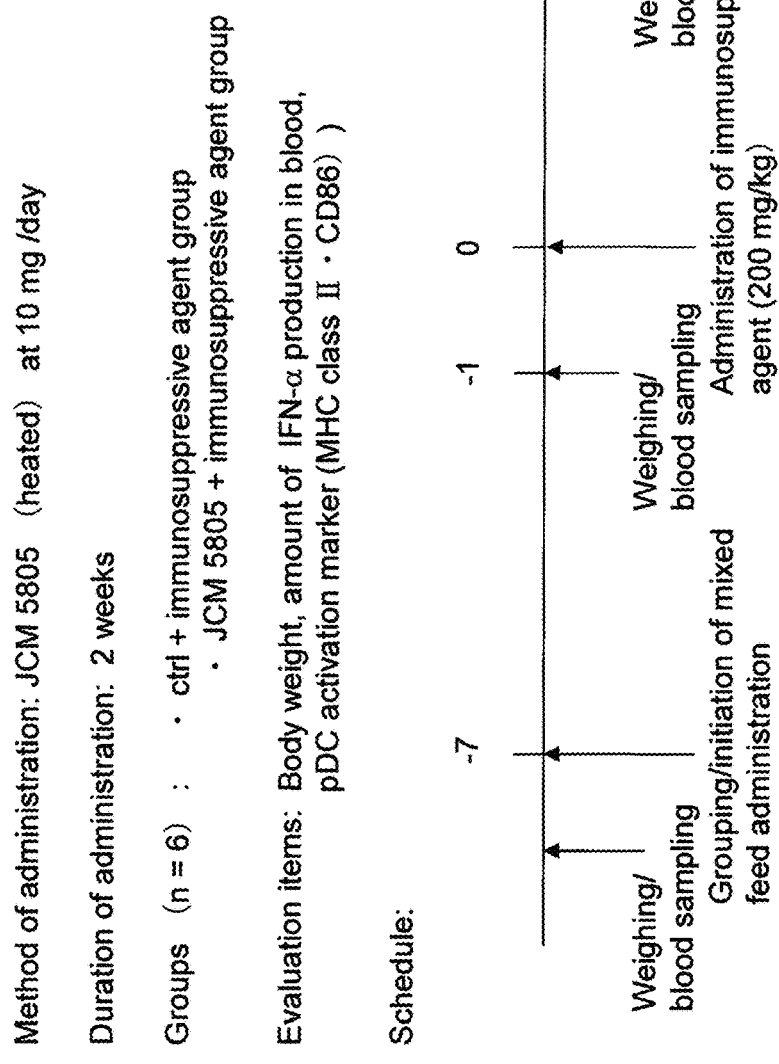
FIG. 14 shows a summary of a method for evaluation of *Lactococcus lactis* JCM5805 using the immunosuppression models.

Two groups of C57BL/6 mice (7-week-old, female) each consisting of 5 individuals were provided: a group to which standard feeds (AIN93G, Oriental Yeast Co., Ltd.) are administered; and a group to which mixed feeds containing *Lactococcus lactis* JCM5805 are administered. The duration for administration of *Lactococcus lactis* JCM5805 was two weeks, the day on which administration of *Lactococcus lactis* JCM5805 was initiated was designated as "day −7," and an immunosuppressive agent (Cyclophosphamide, Sigma-Aldrich) was administered intraperitoneally at 200 mg/kg on day 0. Blood sampling was carried out on day −7, day −1, day 3, and day 7 (at the time of anatomy), and the blood IFN-α levels were assayed in the same manner as in the examples above. Mice were subjected to anatomy at the end and the degree of pDC activation in the spleen was assayed in the same manner as in the examples above. Body weights were measured simultaneously with blood sampling. FIG. 14 shows a summary of a method for evaluation of JCM5805 using immunosuppression models.
<Results>

Figure 15B:
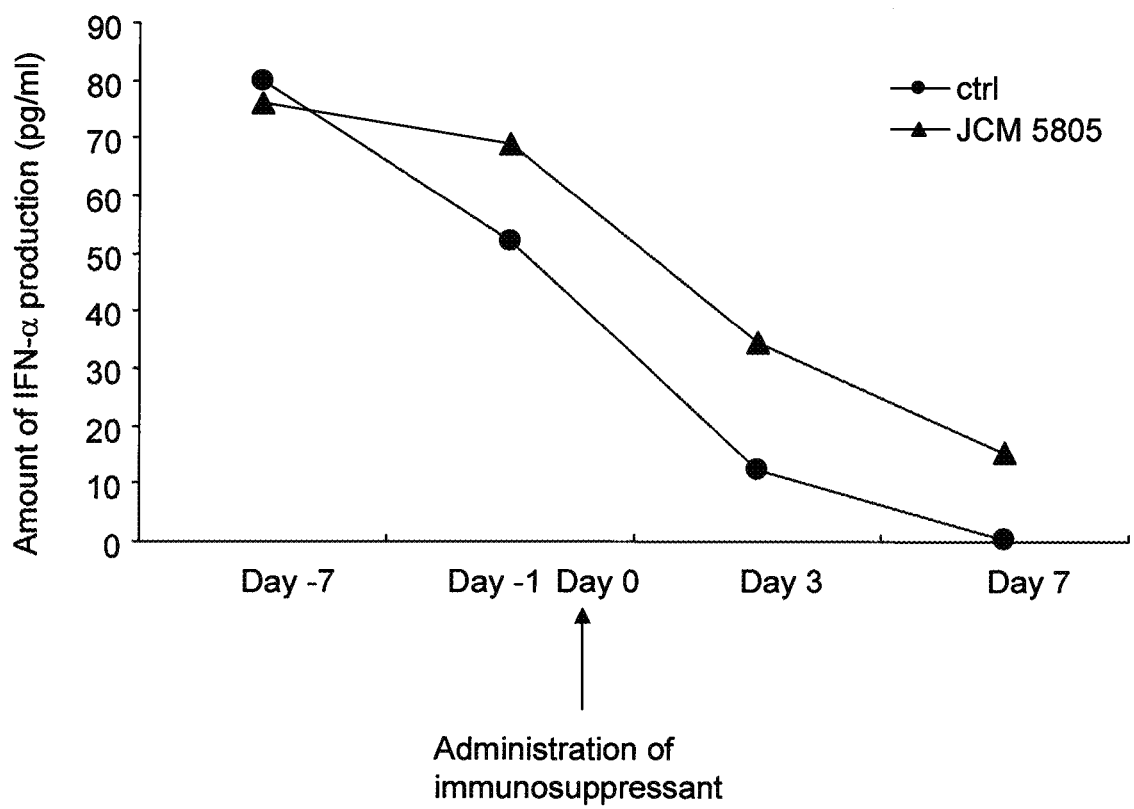
FIG. 15B shows the effects of ingestion of *Lactococcus lactis* JCM5805 using the immunosuppression models with reference to changes in the blood IFN-α levels of mouse models.
Figure 16A:
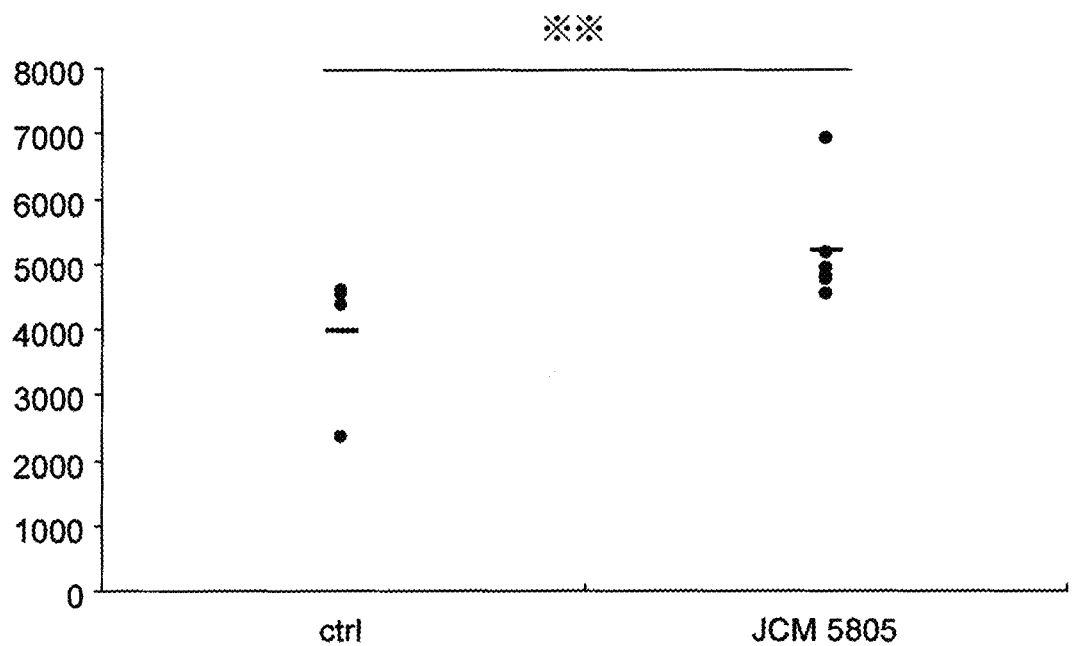
FIG. 16A shows changes in MEW class II levels in pDCs of the immunosuppression mouse models that had ingested *Lactococcus lactis* JCM5805.
Figure 16B:
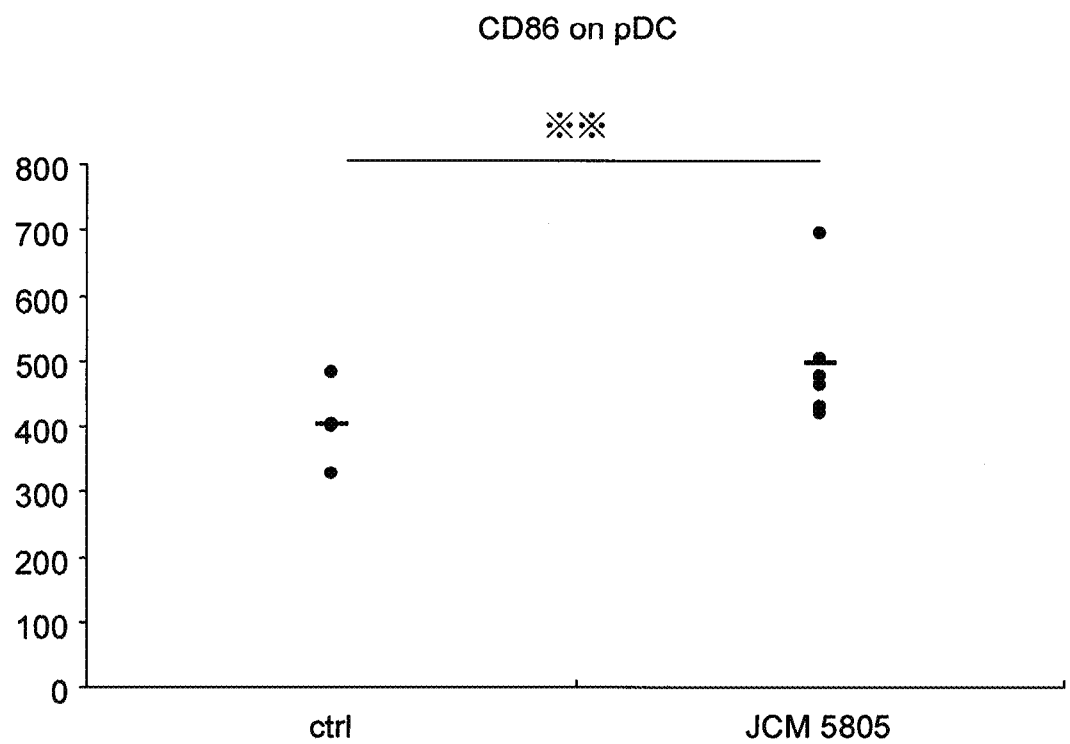
FIG. 16B shows changes in CD86 levels in pDCs of the immunosuppression mouse models that had ingested *Lactococcus lactis* JCM5805.
Figure 16D:
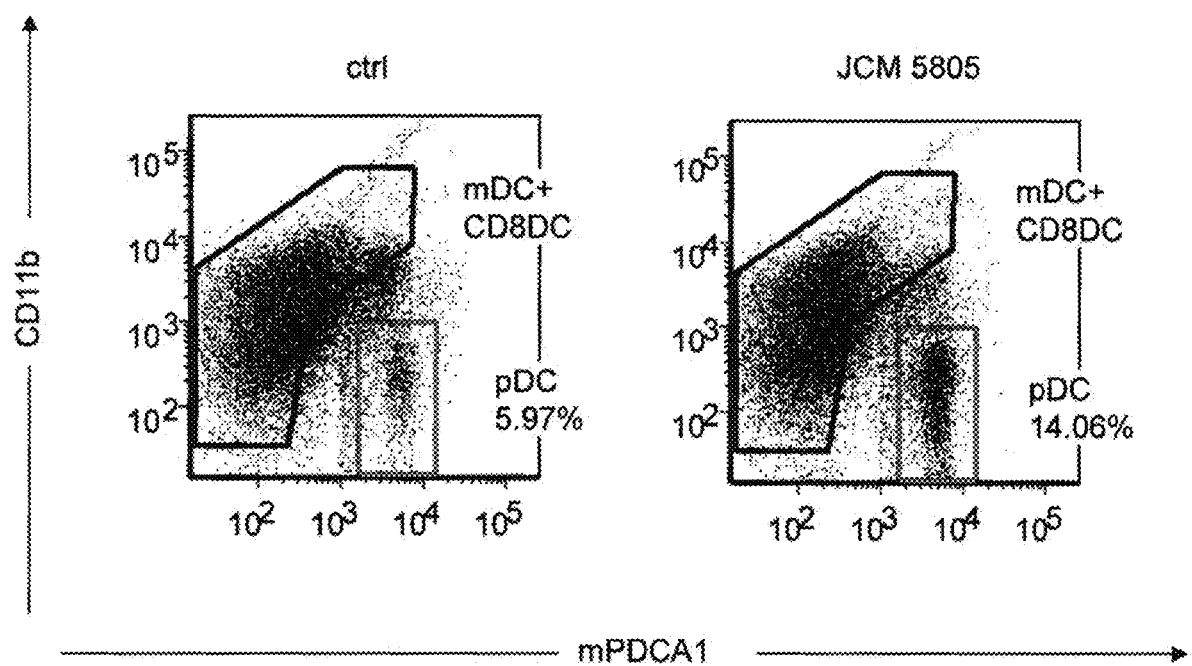
FIG. 16D shows the results of flow cytometric analysis using lymphocytes of the immunosuppression mouse models that had ingested *Lactococcus lactis* JCM5805.

FIG. 15A shows changes in body weights of immunosuppression mouse models and FIG. 15B shows changes in blood IFN-α levels. FIG. 16A shows changes in MHC class II levels in pDCs and FIG. 16B shows changes in CD86 levels in pDCs. FIG. 16C shows a percentage of pDCs and FIG. 16D shows the results of flow cytometric analysis. A significant decrease was observed in body weights of mice of the group to which standard feeds had been administered after the administration of Cyclophosphamide. In contrast, body weight loss tended to be suppressed in the group to which *Lactococcus lactis* JCM5805 had been administered. In the group to which standard feeds had been administered, IFN-α became undetected in the blood at the end; however, IFN-α production was still observed at the time of autopsy in the group to which *Lactococcus lactis* JCM5805 had been administered. As a result of a comparison of the degree of pDC activation in the spleen, MHC class II and CD86 levels significantly increased in the group to which *Lactococcus lactis* JCM5805 had been administered, compared with those in the group to which standard feeds had been administered. More interestingly, a percentage of pDCs in the spleen was significantly increased in the group to which *Lactococcus lactis* JCM5805 had been administered. The above results indicate that orally-ingested *Lactococcus lactis* JCM5805 is able to antagonize immunosuppression induced by stress, aging, or other factors in daily life, and the contribution of such strain to prevention of infections caused by a weakened immune system is significant.

Example 11

Verification of Proper Production of Dairy Products

With the use of the lactic acid bacteria according to the present invention, fermented milk (set yogurt, stirred yogurt) and natural cheese were prepared.

The "set yogurt" is also referred to as a "firm yoghurt" or "still yogurt," which is subjected to fermentation in a container.

The "stirred yogurt" is also referred to as a "fermented yogurt" or "fluid yoghurt," which is subjected to fermentation and then filled into a container.

<Experimental Method>

1. Set Yogurt (Mixed Culture with *Lactobacillus bulgaricus* and *Streptococcus thermophilus*)

(1) As raw materials, raw milk (e.g., milk or skim milk powder), highly-branched cyclic dextrin ("Cluster Dextrin" (tradename), Nihon Shokuhin Kako Co., Ltd.), milk peptide (a general-purpose product), and a yogurt flavor (T. Hasegawa Co., Ltd.) were used.

| Formulation Table 1 | |
| --- | --- |
| | Composition ratio |
| Milk | 60% |
| Skim milk powder | 4.2% |
| Milk peptide | 0.10% |
| Cluster Dextrin | 1.0% |
| Yogurt flavor | 0.03% |
| Lactic acid starter (*L. bulgaricus, St. thermophilus*) | 3.0% |
| Lactic acid starter (*Lc. lactis* JCM5805) | 3.0% |

(2) The raw materials were mixed to prepare a dispersion, the resulting dispersion was heated to about 70° C., and the resultant was applied to a homogenizer at a homogenization pressure (15 to 17 MPa). The resultant was heat-sterilized at 95° C. for about 10 minutes, the resultant was cooled to about 35° C., lactic acid bacteria were added thereto (bacterial species: *L. bulgaricus, St. thermophilus*, and *Lc. lactis* JCM5805), and the resultant was filled into a container with a lid, followed by fermentation at 32° C. for about 6 to 7 hours. When the acidity of lactic acid reached 0.70, the resultant was cooled to 10° C. and stored.

Results:

(1) Flavor: good (2) Lactic acid bacteria count (*Lc. lactis* JCM5805): $10^7$ cells/g or more 2. Set Yogurt (1) As raw materials, raw milk (e.g., milk or skim milk powder), highly-branched cyclic dextrin ("Cluster Dextrin" (tradename), Nihon Shokuhin Kako Co., Ltd.), milk peptide (a general-purpose product), and a yogurt flavor (T. Hasegawa Co., Ltd.) were used.

| Formulation Table 2 | |
| --- | --- |
| | Composition ratio |
| Milk | 60% |
| Skim milk powder | 4.2% |
| Milk peptide | 0.10% |
| Cluster Dextrin | 1.0% |
| Yogurt flavor | 0.03% |
| Lactic acid starter (*Lc. lactis* JCM5805) | 6.0% |

(2) The raw materials were mixed to prepare a dispersion, the resulting dispersion was heated to about 70° C., and the resultant was applied to a homogenizer at a homogenization pressure (15 to 17 MPa). The resultant was heat-sterilized at 95° C. for about 10 minutes, the resultant was cooled to about 35° C., lactic acid bacteria were added thereto (bacterial species: *Lc. lactis* JCM5805), and the resultant was filled into a container with a lid, followed by fermentation at 32° C. for about 16 hours. When the acidity of lactic acid reached 0.70, the resultant was cooled to 10° C. and stored.

Results:

(1) Flavor: good (2) Lactic acid bacteria count (*Lc. lactis* JCM5805): $10^7$ cells/g or more 3. Stirred Yogurt (1) As raw materials, raw milk (e.g., milk or skim milk powder), highly-branched cyclic dextrin ("Cluster Dextrin" (tradename), Nihon Shokuhin Kako Co., Ltd.), milk peptide (a general-purpose product), and a yogurt flavor (T. Hasegawa Co., Ltd.) were used.

| Formulation Table 3 | |
| --- | --- |
| | Composition ratio |
| Milk | 60% |
| Skim milk powder | 4.2% |
| Milk peptide | 0.10% |
| Cluster Dextrin | 1.0% |
| Yogurt flavor | 0.03% |
| Lactic acid starter (*Lc. lactis* JCM5805) | 4.0% |

The raw materials were mixed to prepare a dispersion, the resulting dispersion was heated to about 70° C., and the resultant was applied to a homogenizer at a homogenization pressure (15 to 17 MPa). The resultant was heat-sterilized at 125° C., the resultant was cooled to about 35° C., and lactic acid bacteria were added thereto (bacterial species: *Lc. lactis* JCM5805), followed by fermentation at 32° C. for about 16 hours. Fermentation was terminated at pH 4.6, the product was cooled to about 20° C., and the resultant was filled into a container with stirring, followed by refrigeration at 10° C. or lower.

Results:

(1) Flavor: good (2) Lactic acid bacteria count (*Lc. lactis* JCM5805): $10^7$ cells/g or more 4. Drinkable Yogurt (1) As raw materials, raw milk (e.g., milk or skim milk powder), highly-branched cyclic dextrin ("Cluster Dextrin" (tradename), Nihon Shokuhin Kako Co., Ltd.), milk peptide (a general-purpose product), and a yogurt flavor (T. Hasegawa Co., Ltd.) were used.

Formulation Table 4

|  | Composition ratio |
|---|---|
| Milk | 30% |
| Skim milk powder | 6% |
| Milk peptide | 0.20% |
| Cluster Dextrin | 1.0% |
| Sugar | 8% |
| Yogurt flavor | 0.03% |
| Lactic acid starter (*Lc. lactis* JCM5805) | 6.0% |

(2) The raw materials were mixed to prepare a dispersion, the resulting dispersion was heated to about 70° C., and the resultant was applied to a homogenizer at a homogenization pressure (15 to 17 MPa). The resultant was heat-sterilized at 125° C., the resultant was cooled to about 35° C., and lactic acid bacteria were added thereto (bacterial species: *Lc. lactis* JCM5805), followed by fermentation at 32° C. for about 16 hours. Fermentation was terminated at pH 4.6, the product was cooled to about 10° C., and the resultant was homogenized (in vacuo), followed by refrigeration at 10° C. or lower.
Results:
(1) Flavor: good
(2) Lactic acid bacteria count (*Lc. lactis* JCM5805): $10^7$ cells/g or more
5. Natural Cheese
(1) As raw materials, raw milk (i.e., milk), rennet (Standard Plus290, Christian Hansen), and calcium chloride (a general-purpose product) were used.

Formulation Table 5

| Raw materials | Single strain |
|---|---|
| Milk | 100% |
| Lactic acid starter (*Lc. lactis* JCM5808) | 3% |
| Rennet | 0.003% |
| 20% calcium chloride | 0.0025% |
| Whey removed | −50% |

(2) Raw milk was heat-sterilized at 75° C. for 15 seconds, the resultant was cooled to about 30° C., and lactic acid bacteria were added thereto (bacterial species: *Lc. lactis* JCM5805), followed by fermentation at 30° C. for about 1 hour. Fermentation was terminated at pH 6.4 and acidity of about 0.13, calcium chloride and rennet (Standard Plus290, Christian Hansen) were added, the mixture was stirred for about 3 minutes, and formation of curds was confirmed 30 minutes later. The curds were cut into sizes of about 1 to 2 cm squares. The whey was removed, the curds were packed into a mold, and the mold was inverted several times and allowed to stand for 12 hours.

The moisture content of the product was adjusted with pressurization by applying the weight that is about 10 times greater than that of the curds packed into the mold.
Results:
(1) Flavor: good
(2) Lactic acid bacteria count (*Lc. lactis* JCM5805): 10' cells/g or more Example 12

Effects of Live *Lactococcus lactis* JCM5805, *Lactococcus lactis* 20101, and *Lactobacillus rhamnosus* ATCC53103

According to the examples above, activity of heat-killed bacteria is known; however, whether or not live bacteria would act on pDCs remains unknown. Thus, effects of live *Lactococcus lactis* JCM5805, *Lactococcus lactis* 20101, and *Lactobacillus rhamnosus* ATCC53103 on mouse pDCs were inspected using the pDC/mDC culture system.
<Experimental Method>
Preparation of Live Lactic Acid Bacteria In accordance with the procedure of Example 1, *Lactococcus lactis* JCM5805, *Lactococcus lactis* JCM20101, and *Lactobacillus rhamnosus* ATCC53103 were subjected to stationary culture. The strains were harvested, washed three times with sterile water, and then suspended in PBS. The lactic acid bacteria count was determined using a particle size distribution measuring device (CDA-1000X, Sysmex Corporation), the cells were added to the pDC/mDC culture system at concentrations of $1\times10^6$, $1\times10^7$, and $1\times10^8$ cells, and culture was conducted in a $CO_2$ incubator for 48 hours. The culture supernatant was recovered, and the amount of IFN-α produced in the culture supernatant was assayed.
<Results>

Figure 18:
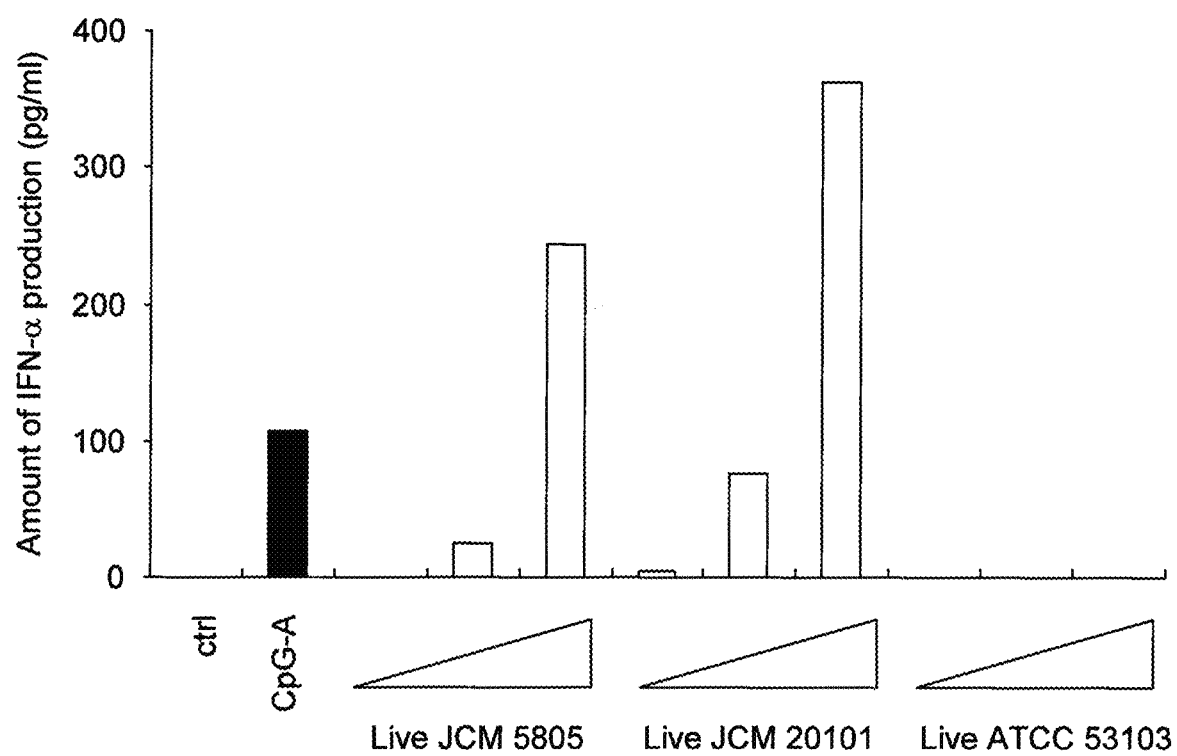
FIG. 18 shows the capacity of live *Lactococcus lactis* JCM5805, *Lactococcus lactis* JCM20101, and *Lactobacillus rhamnosus* ATCC53103 for IFN-α activation.

The results are shown in FIG. 18. While live *Lactococcus lactis* JCM5805 and JCM20101 induced IFN-α production in a bacterial-count-dependent manner, live *Lactobacillus rhamnosus* ATCC53103 did not induce IFN-α production at all. Regardless of whether or not the *Lactococcus lactis* JCM5805 and JCM20101 strains are heat-killed or alive, these strains were found to activate pDCs and potently induce IFN-α production.

Example 13

Activity of *Lactococcus lactis* JCM5805 on Human pDC

In the examples above, lactic acid bacteria capable of acting on mouse pDC were found; however, whether or not such bacteria were capable of acting on human pDCs was unknown. Thus, pDCs were isolated from human PBMCs with MACS, JCM5805 was designated as a representative sample, and activity thereof on human pDCs was inspected.
<Experimental Method>

PBMCs were purchased from LONZA.
pDC Isolation with MACS and Purity Inspection

In accordance with the protocols of the Plasmacytoid Dendritic Cell Isolation Kit (Miltenyi Biotec), human pDCs were isolated with MACS (purity: 97%). Human pDCs ($5\times10^4$ cells) were cultured on a 96-well flat-bottom plate (Corning). To the isolated human pDCs, IL-3 (R&D Systems) was added at 10 ng/ml as the survival factor. In order to inspect the purity of human pDCs, human pDCs were stained with anti-CD123-FITC (AC145) antibody and anti-BDCA4-APC (AD-17F6) antibody (Miltenyi Biotec) for human pDC gating and then analyzed using the FACS Canto II (BD).
Addition of Ligand, Cell Culture, and ELISA

*Lactococcus lactis* JCM5805 was added to a final concentration of 10 μg/ml, and culture was conducted in a $CO_2$ incubator for 24 hours. Human IFN-α levels were assayed using the Human IFN-α ELISA Kit (PBL Biomedical Laboratories).
Analysis of IFN Gene Expression Via RT-PCR The cultured cells were recovered, and total RNAs were extracted using the RNeasy Mini Kit (Qiagen). cDNA was synthesized from 200 ng of total RNA using the iScript cDNA Synthesis Kit (Bio-Rad), and IFN-α1, IFN-λ1, and GAPDH genes were amplified via PCR using the synthesized cDNA as a template. PCR was carried out using TaKaRa Ex Taq (TaKaRa) and the primers described in Non-Patent Document 7. In accordance with general protocols, IFN-α1, IFN-β, IFN-λ1, and GAPDH genes were subjected to the reaction at 94° C. for 1 minute, and a cycle of 94° C. for 30 seconds, at 49° C., 45° C., 49° C., and 45° C. for 30 seconds, respectively, and 72° C. for 15 seconds repeated 35 times, followed by the reaction at 72° C. for 3 minutes. The PCR reaction solution was electrophoresed in accordance with a general technique, and development of amplified fragments and the density thereof were inspected.

<Results>

Figure 19A:
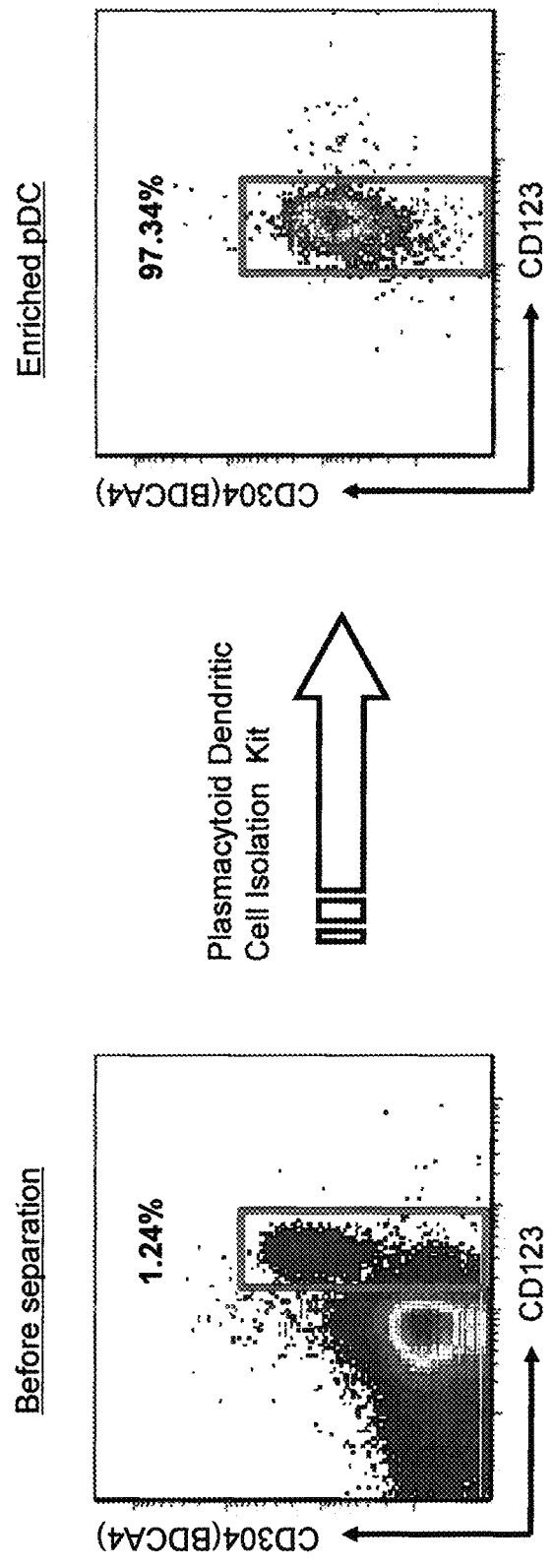
FIG. 19A shows the percentage of pDCs determined by flow cytometric analysis of the purity of human pDCs isolated with MACS.
Figure 19B:
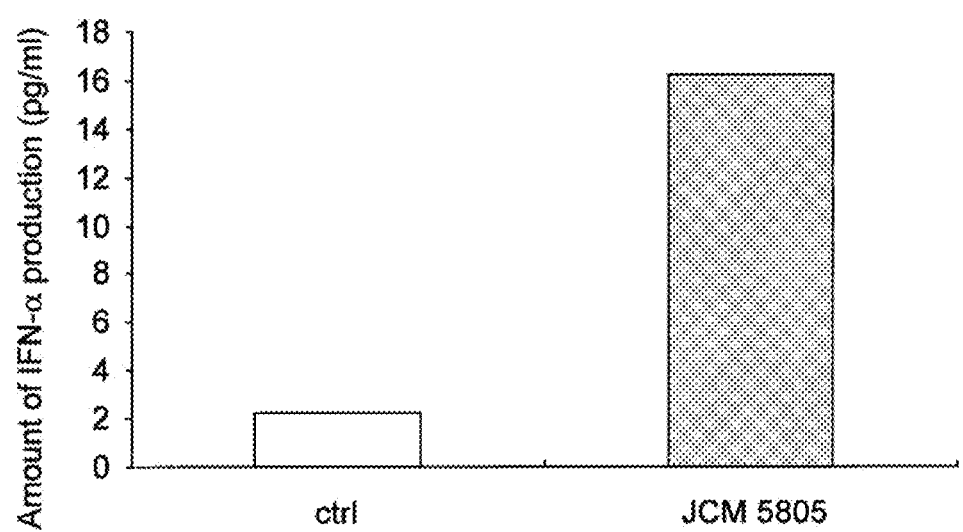
FIG. 19B shows the amount of IFN-α production detected via ELISA when *Lactococcus lactis* JCM5805 is added to human pDCs isolated with MACS.
Figure 19C:
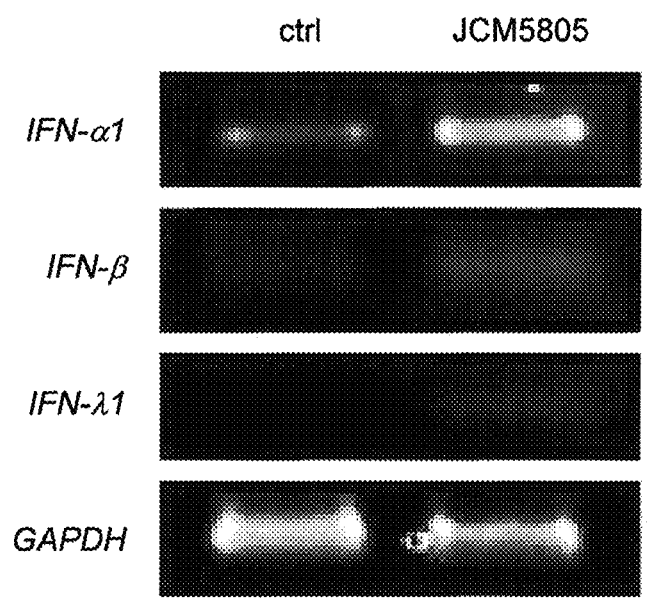
FIG. 19C shows IFN-α1, IFN-β, IFN-λ1, and GAPDH gene expression detected via RT-PCR when *Lactococcus lactis* JCM5805 is added to human pDCs isolated with MACS.
Figure 20A:
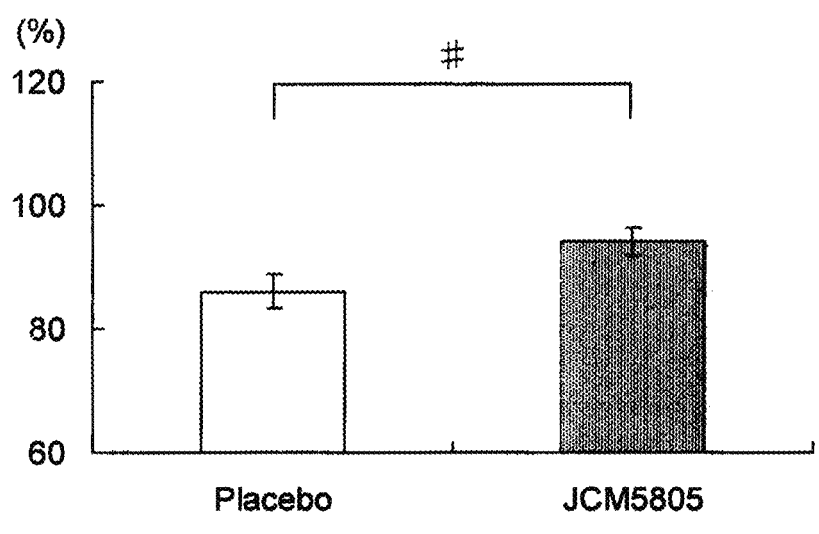
FIG. 20A shows a comparison of changes in MHC class II activity in pDCs of the group subjected to ingestion of yogurt containing *Lactococcus lactis* JCM5805 and of the placebo group.
Figure 20B:
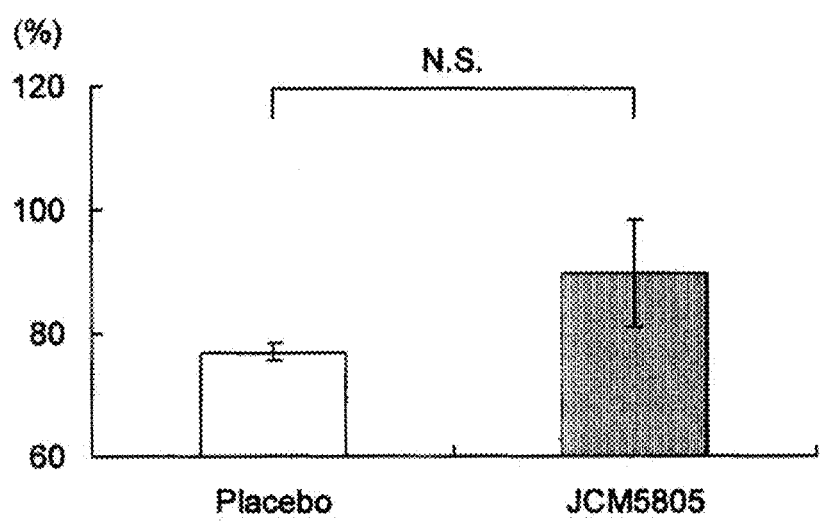
FIG. 20B shows a comparison of changes in MHC class II activity in pDCs of a subject having high MHC class II activity in the group subjected to ingestion of yogurt containing *Lactococcus lactis* JCM5805 and in the placebo group.
Figure 20C:
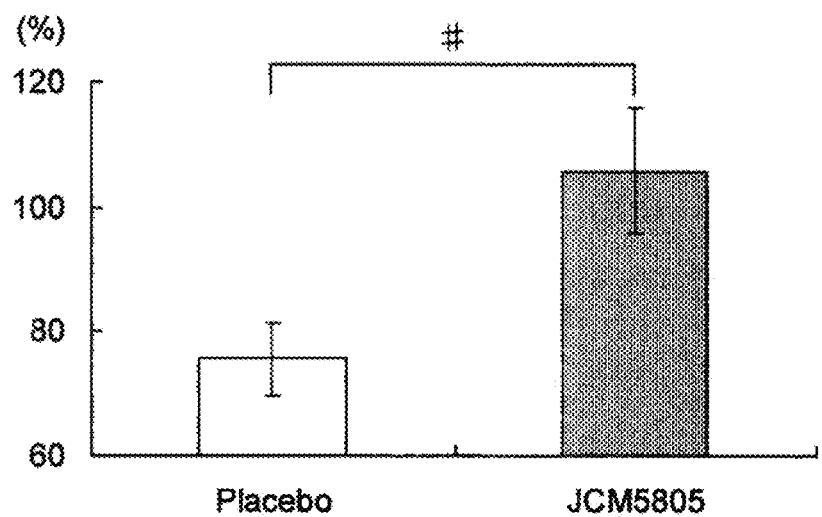
FIG. 20C shows a comparison of changes in MHC class II activity in pDCs of a subject having low MHC class II activity in the group subjected to ingestion of yogurt containing *Lactococcus lactis* JCM5805 and in the placebo group.
Figure 20D:
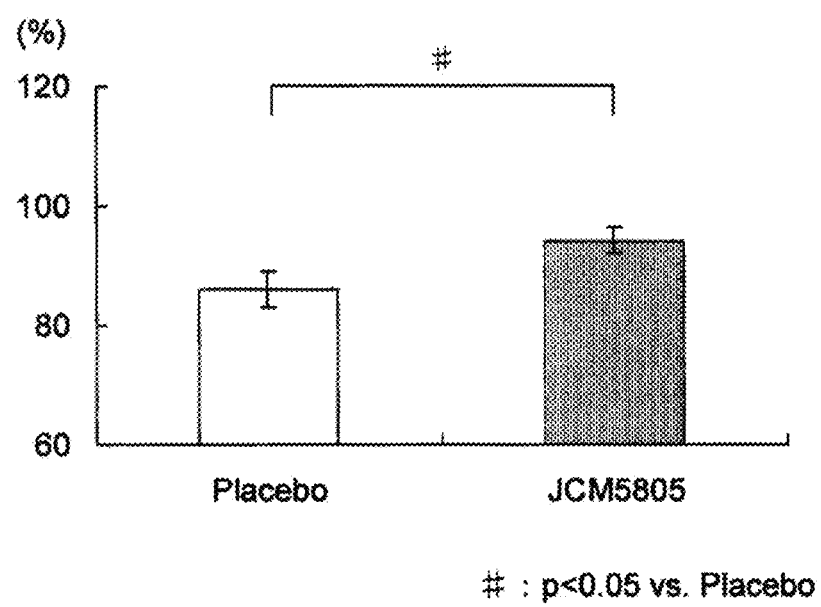
FIG. 20D shows a comparison of changes in CD86 activity in pDCs of the group subjected to ingestion of yogurt containing *Lactococcus lactis* JCM5805 and of the placebo group.
Figure 20E:
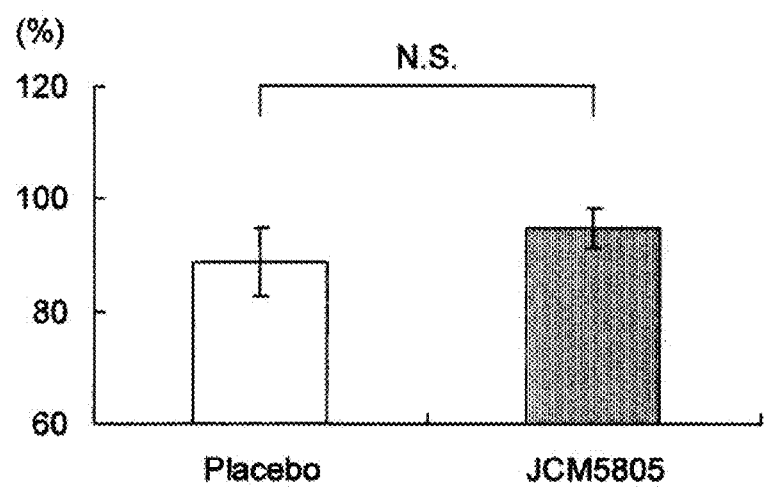
FIG. 20E shows a comparison of changes in CD86 activity in pDCs of a subject having high MHC class II activity in the group subjected to ingestion of yogurt containing *Lactococcus lactis* JCM5805 and in the placebo group.
Figure 20F:
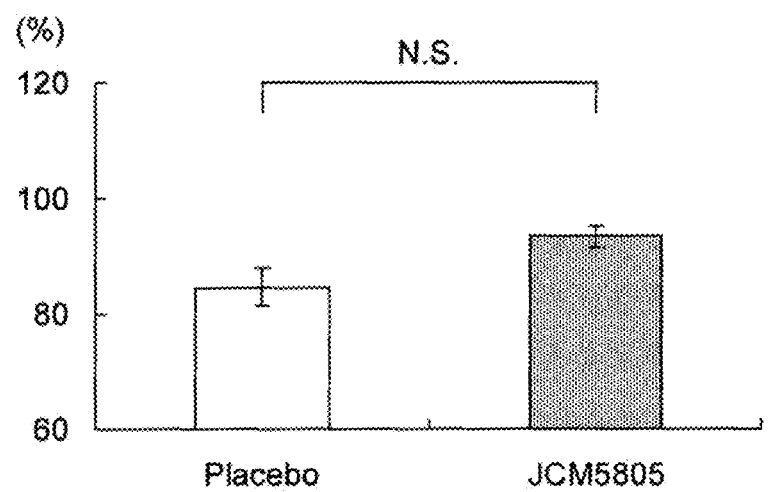
FIG. 20F shows a comparison of changes in CD86 activity in pDCs of a subject having low MHC class II activity in the group subjected to ingestion of yogurt containing *Lactococcus lactis* JCM5805 and in the placebo group.

The results are shown in FIG. 19. FIG. 19A, FIG. 19B, and FIG. 19C show the purity of human pDCs isolated with MACS, the amount of IFN-α production detected at the protein level by ELISA, and IFN-α1, IFN-β, IFN-λ, and GAPDH gene expression levels detected by RT-PCR. With the addition of *Lactococcus lactis* JCM5805, induction of IFN-α production was observed at the protein level. Also, induction of IFN-α1, IFN-β, and IFN-λ, gene expression was detected. The above results demonstrate that *Lactococcus lactis* JCM5805 would also activate human pDCs.

Example 14

Influence of Yogurt Containing *Lactococcus lactis* JCM5805 on Human Antiviral Activity In the examples above, effects of *Lactococcus lactis* JCM5805 on mouse and human cells in vitro and effects thereof attained upon ingestion by mice were verified. On the basis of such results, effects attained upon ingestion by humans were examined.

<Outline of Testing>

Test Foods

Two types of test products described below were used.
(1) Test product: yogurt drink containing *Lactococcus lactis* JCM5805
(2) Placebo product: yogurt-like drink containing no lactic acid bacteria Purpose:

This test was carried out aimed at examination of the influence of lactic acid bacteria on blood biomarkers associated with antiviral activity and on subjective evaluation by questionnaires concerning physical conditions of healthy, working, adult males and females who had continuously ingested yogurt drinks containing *Lactococcus lactis* JCM5805s for about 4 weeks, in comparison with the control experiment conducted with the use of yogurt-like drinks containing no lactic acid bacteria as placebos.

Test Subjects:

Test subjects were those who had no serious chronic disease, milk allergy, or other conditions, those who were evaluated to have no problem by a particular virus test, those who were capable of restricting intake of yogurt and cheese during the period of test product ingestion, and those who were not on steroid medications (internal or external use).

Number of Subjects:

Thirty eight subjects (two groups each consisting of 19 subjects) were employed.

Test Design:

A randomized, double-blind, placebo-controlled, parallel-group study was carried out.

Amount of Test Component to be Ingested Per Day:

A daily dose was about $1 \times 10^{11}$ cfu of *Lactococcus lactis* JCM5805.

Ingestion Method

Test subjects were asked to drink a bottle of the test product (100 ml) before or after meal in the morning every day.

Test Schedule

The period of test product ingestion was about 4 weeks. Blood sampling was carried out three times: at a pre-test for grouping (1 month before the initiation of ingestion); at week 0 (the day before the initiation of ingestion); and at week 4 (the day after the termination of ingestion). Test subjects answered the questionnaires concerning physical conditions every day during the ingestion period.

Evaluation Items pDC activity in the blood (pDC surface markers: MHC class II and CD86), IFN-α gene expression in the blood, and the capacity for IFN-α production upon stimulation of peripheral blood mononuclear cells (PBMCs) with CpG DNA were assayed, and subjective evaluation of cold symptoms was carried out in accordance with the questionnaires concerning physical conditions.

<Experimental Method>

Blood biomarkers were analyzed by isolating PBMCs from the blood samples obtained on week 0 and week 4 and examining the isolated PBMCs.

PBMCs ($1 \times 10^6$ cells) were stained with anti-CD123-FITC (AC145) (Miltenyi Biotec), anti-BDCA4-APC (AD-17F6) (Miltenyi Biotec), anti-CD86-PE (B7.2) (eBioscience), and anti-HLA-DR-PerCP (L243) (BD Biosciences) in accordance with a conventional technique. HLA-DR (MHC class II) and CD86 fluorescent intensities of the cell populations detected in CD123$^+$/BDCA4$^+$ were assayed with the use of FACS Canto II (BD), and the determined values were employed as the indicators for pDC activation.

IFN-α gene expression in the blood was detected by extracting total RNAs from $1 \times 10^6$ PBMCs using the RNeasy Mini Kit (Qiagen). cDNA was synthesized from 100 ng of total RNA using the iScript cDNA Synthesis Kit (Bio-Rad), and the IFN-α1 gene (the GAPDH gene as a reference) was analyzed via real-time PCR using the synthesized cDNA as a template. Real-time PCR analysis was carried out using SYBR Premix Ex Taq (TaKaRa) and the primers described in Non-Patent Document 7. In accordance with general protocols, the samples were subjected to the reaction at 95° C. for 10 seconds, followed by a cycle of 95° C. for 10 seconds, 49° C. for 5 seconds, and 72° C. for 10 seconds repeated 50 times.

In order to inspect the capacity for IFN-α production upon stimulation of the blood pDCs with CpG DNA, $5 \times 10^5$ PBMCs were seeded on a 24-well flat-bottom plate (Corning), and CpG-ODN2216 (CpG-A) (InvivoGen) was added thereto to the final concentration of 0.5 μM/ml. With respect to all the samples obtained from subjects, control samples containing no CpG DNA were prepared. Culture was conducted in a $CO_2$ incubator at 37° C. for 24 hours, the supernatant was recovered, and the amount of IFN-α production was assayed using the human IFN-α matched antibody pairs for ELISA (eBioscience).

When *Streptococcus pyogenes* or influenza virus was allowed to act on human pDCs in vitro, the MHC class II expression level was elevated with a good response, although no significant increase was observed in the CD86 expression level (Non-Patent Document 8). Accordingly, MHC class II was designated as a major activation marker, and 36 samples exhibiting values of average MHC class II activity ±2SD (18 samples from each group) were subjected to analyses of all biomarkers. The samples were divided into those exhibiting values higher than the average MHC class II activity assayed at week 0 (hereafter referred to as "higher pDC activity") and those exhibiting values lower than such average (hereafter referred to as "lower pDC activity"), and these samples were separately analyzed.

In the questionnaires concerning physical conditions, 7 main cold symptoms (i.e., runny nose, stuffy nose, sneezing, sore throat, itchy throat, coughing, headache, and fever) were rated using a 5-point scale (from 1: no symptom, to 5: severe symptom) every day. The average of the 7 items was designated as the indicator for the severity of cold symptoms.

<Results>

The results of assays for pDC activity in the blood are shown in FIG. 20. FIG. 20A and FIG. 20D show changes in MHC class II and CD86 activity in pDCs observed in the activity assays from week 0 to week 4. Changes in MHC class II and CD86 activity of the group that had ingested yogurt drinks containing *Lactococcus lactis* JCM5805 (hereafter, referred to as "the JCM5805 group") were significantly higher than those of the group that had ingested yogurt-like drink containing no lactic acid bacteria (hereafter, referred to as "the placebo group"). The results of analyses separately conducted for the samples exhibiting higher pDC activity and for the samples exhibiting lower pDC activity and the changes in MHC class II activity are shown in FIG. 20B and FIG. 20C, respectively. The results as mentioned above and the changes in CD86 activity are shown in FIG. 20E and FIG. 20F, respectively. Regarding changes in MHC class II activity, there was no significant difference in samples exhibiting higher pDC activity between the JCM5805 group and the placebo group. In the case of samples exhibiting lower pDC activity, however, such changes of the JCM5805 group were significantly higher than those of the placebo group. Regarding changes in CD86 activity, no significant difference was observed between the JCM5805 group and the placebo group, regardless of pDC activity levels. This is considered to occur because CD86 is less likely to be influenced by pDC activity, as described in Non-Patent Document 8. The above results demonstrate that pDC activity is elevated upon ingestion of *Lactococcus lactis* JCM5805 and that the effects are more significant for subjects exhibiting lower pDC activity and having a weaker immune system.

Figure 21:
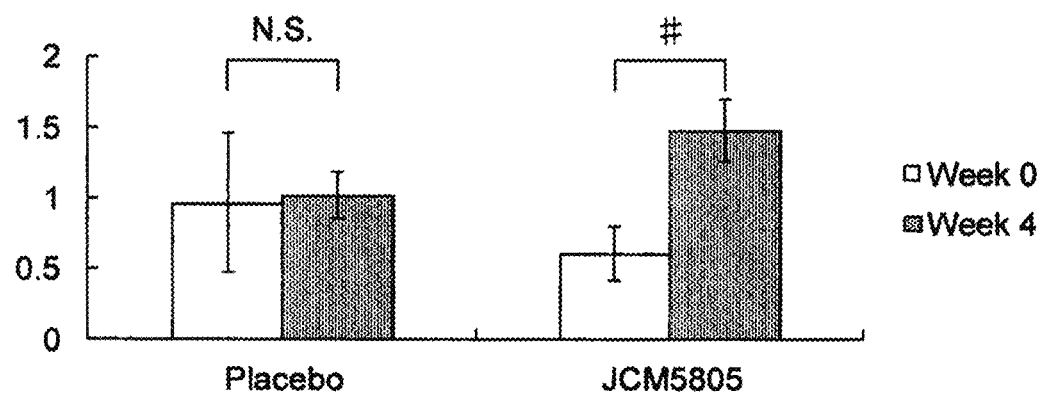
FIG. 21 shows a comparison of amounts of IFN-α1 gene transcription in PBMCs compared at week 0 and week 4 after the initiation of the test of a subject having low MHC class II activity in the group subjected to ingestion of yogurt containing *Lactococcus lactis* JCM5805 and in the placebo group.

FIG. 21 shows the results of analysis of IFN-α gene expression in the blood at lower pDC activity. At lower pDC activity, no significant changes were observed from week 0 to week 4 in the placebo group; however, a significant increase was observed in expression levels from week 0 to week 4 in the JCM5805 group. At higher pDC activity, no significant changes were observed from week 0 to week 4 in the placebo group and in the JCM5805 group (data not shown). The results demonstrate that the amount of IFN-α gene transcription in the human blood is increased by ingestion of *Lactococcus lactis* JCM5805.

Figure 22:
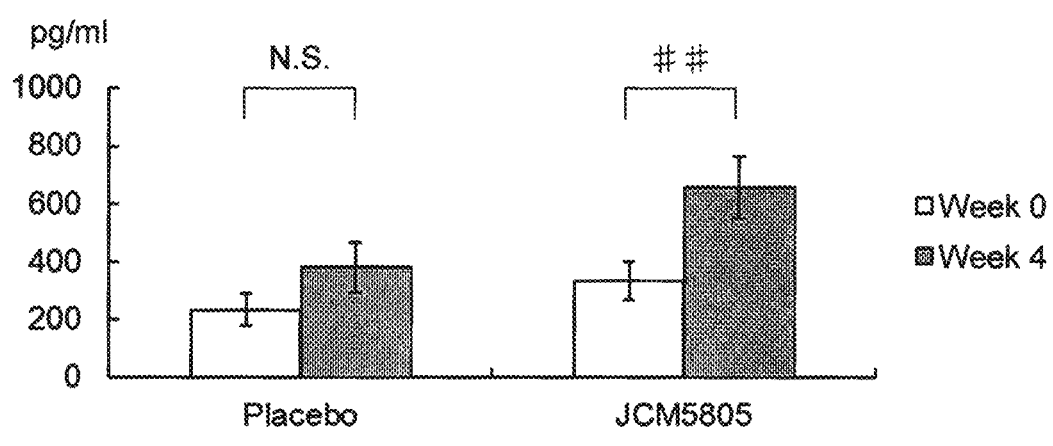
FIG. 22 shows a comparison of amounts of IFN-α production influenced by CpG stimulation in PBMCs compared at week 0 and week 4 after the initiation of the test of a subject having low MHC class II activity in the group subjected to ingestion of yogurt containing *Lactococcus lactis* JCM5805 and in the placebo group.

FIG. 22 shows the results of assays for the capacity for IFN-α production attained when the blood pDCs exhibiting lower pDC activity are stimulated with CpG DNA. At lower pDC activity, no significant changes were observed from week 0 to week 4 in the placebo group; however, a significant increase was observed from week 0 to week 4 in the JCM5805 group. At higher pDC activity, no significant changes were observed from week 0 to week 4 in the JCM5805 group (data not shown). CpG DNA is a nucleic acid ligand targeting TLR9, and the virus recognition mechanism of pDC detects viral DNA or RNA by means of TLR9 or TLR7/8. Accordingly, the virus recognition mechanism was wrongly stimulated by addition of a nucleic acid ligand (i.e., CpG DNA). Specifically, the results of the experiments indicate that pDC activation induced by CpG DNA stimulation is potentiated in the JCM5805 group and it leads to an enhanced response at the time of virus infection.

FIG. 23 shows the results of the questionnaires concerning physical conditions. For the JCM5805 group and the placebo group, the total number of days during which cold symptoms had developed and the total number of days during which cold symptoms did not develop were determined in every week, and the outcomes were subjected to the square test. As a result, the total number of days during which the subjects in the JCM5805 group had developed cold symptoms was found to be significantly fewer, and the total number of days during which the subjects did not develop cold symptoms was found to be larger on week 4, compared with the placebo group. This indicates that continuous ingestion of *Lactococcus lactis* JCM5805 for 4 weeks leads the subjects to be less susceptible to colds.

The above results demonstrate that blood pDCs are activated when human ingests *Lactococcus lactis* JCM5805, the capacity for IFN-α production is enhanced, and responses upon virus infection are improved, which would consequently lead a person to be less susceptible to colds. Such effects were particularly significant for subjects with lower immunity against virus infection (pDC activity) and at a high risk of catching a cold.

All publications, patents, and patent applications cited herein are incorporated herein by reference in their entirety.

INDUSTRIAL APPLICABILITY

Lactic acid bacteria capable of activating pDCs and inducing IFN production can be used for an immunostimulatory pharmaceutical product or food or drink product as the agent for inducing IFN production.

The invention claimed is:

1. A method for preventing cold symptoms, comprising administering to the subject a lactic acid bacteria that is capable of activating plasmacytoid dendritic cells (pDCs) and inducing IFN production, wherein the lactic acid bacteria is *Lactococcus lactis* subsp. *lactis* (Lister) Schleifer et al. (1986), deposited with Japan Collection of Microorganisms of Riken BioResource Center, under Accession No. JCM5805.

2. The method according to claim 1, wherein the lactic acid bacteria is orally administered.

* * * * *